United States Patent
Sato

(10) Patent No.: US 7,125,999 B2
(45) Date of Patent: Oct. 24, 2006

(54) PROCESS FOR PRODUCING ORGANOTITANIUM COMPOUND AND PROCESS FOR ADDITION REACTION

(75) Inventor: Fumie Sato, Fujisawa (JP)

(73) Assignee: Nissan Chemical Industies, Ltd., Tokyo (JP)

( * ) Notice: Subject to any disclaimer, the term of this patent is extended or adjusted under 35 U.S.C. 154(b) by 283 days.

(21) Appl. No.: 10/786,150

(22) Filed: Feb. 26, 2004

(65) Prior Publication Data

US 2004/0167344 A1    Aug. 26, 2004

Related U.S. Application Data

(62) Division of application No. 10/013,453, filed on Dec. 13, 2001, now Pat. No. 6,743,916.

(30) Foreign Application Priority Data

Jun. 15, 2001    (JP)    ............................... 2001-182554

(51) Int. Cl.
*C07F 7/28*    (2006.01)
*C07F 7/102*    (2006.01)
*C07D 211/78*    (2006.01)

(52) U.S. Cl. ........................... 546/4; 546/10; 548/108; 549/3; 549/212; 556/12; 556/52

(58) Field of Classification Search ................. 556/12, 556/52; 546/4, 10; 548/108; 549/3, 212
See application file for complete search history.

(56) References Cited

OTHER PUBLICATIONS

Saito, Chem. Rev., vol. 100, No. 8, pp. 2901-2915 (2000).
Wakatsuki, J. Chem. Soc., Dalton, pp. 1278-1282 (1978).
Takahashi, J. Am. Chem. Soc., vol. 122, No. 20, pp. 4994-4995 (2000).

*Primary Examiner*—Bernard Dentz
(74) *Attorney, Agent, or Firm*—Birch, Stewart, Kolasch & Birch, LLP

(57) ABSTRACT

A process for producing an organotitanium compound capable of regioselectively converting a substituted acetylene compound into polysubstituted benzene or polysubstituted pyridine. The process comprises reacting an acetylene compound represented by the formula (1)

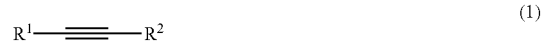

(1)

[where $R^1$ and $R^2$ denote a $C_{1-20}$ alkyl group or the like] in the presence of a prescribed titanium compound and a Grignard reagent with a compound represented by the formula (4)

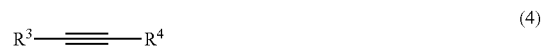

(4)

[where $R^3$ and $R^4$ denote a hydrogen atom or the like] and further reacting with a compound represented by the formula (5)

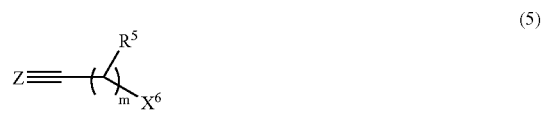

(5)

[where $R^5$ denotes a hydrogen atom or the like, Z denotes CR' (where R' denotes a hydrogen atom or the like), nitrogen atom, $X^6$ denotes a halogen atom or the like, and m is 0 or 1]
thereby giving the titanium compound represented by the formula (6) and/or (7).

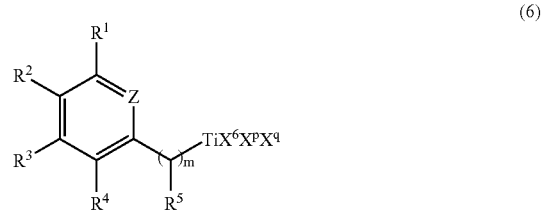

(6)

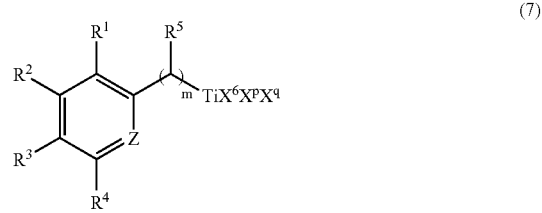

(7)

[where $R^1$~$R^5$, Z, $X^6$, and m are defined as above; and $X^p$ and $X^q$ denote any of $X^1$~$X^4$].

5 Claims, No Drawings

PROCESS FOR PRODUCING ORGANOTITANIUM COMPOUND AND PROCESS FOR ADDITION REACTION

This application is a Divisional of application Ser. No. 10/013,453, filed on Dec. 13, 2001 now U.S. Pat. No. 6,743,916, the entire contents of which are hereby incorporated by reference and for which priority is claimed under 35 U.S.C. § 120; and this application claims priority of Application No. 2001-182554 filed in Japan on Jun. 15, 2001 under 35 U.S.C. § 119.

BACKGROUND OF THE INVENTION

The present invention relates to a process for producing an organotitanium compound useful for production of pharmaceuticals and agricultural chemicals and their intermediates and also to a process for addition reaction involving the organotitanium compound. More particularly, the present invention relates to a process for producing an organotitanium compound useful for production of polysubstituted benzene or polysubstituted pyridine.

There is an established process known as Reppe reaction for producing a benzene compound directly from three acetylene compounds in the presence of a catalyst of transition metal catalyst. This reaction, however, has difficulty in producing a polysubstituted benzene compound regioselectively from substituted acetylene compounds.

As for regioselective production of a substituted benzene compound from three acetylene compounds, several processes are disclosed in Chem. Rev. 2000, 100, 2901–2915. These processes are based on condensation of one molecule of diyne compound and one molecule of acetylene compound. Nothing is mentioned about the process of producing a substituted benzene compound regioselectively from three molecules of acetylene compound.

There is known a process for producing a pyridine compound regioselectively from two acetylene compounds and one nitrile compound. (J. Chem. Soc., Dalton 1978, 1278–1282, J. Am. Chem. Soc. 2000, 122, 4994–4995)

The process disclosed in the former literature has the disadvantage of requiring an expensive cobalt complex and being incapable of using two acetylene compounds of different kind. The process disclosed in the latter literature has the disadvantage of requiring an expensive zirconium catalyst and also requiring two-stage reactions with different catalysts. Therefore, both processes are not suitable for industrial production.

SUMMARY OF THE INVENTION

The present invention was completed in view of the foregoing. Accordingly, it is an object of the present invention to provide a process for producing an organotitanium compound capable of regioselectively converting a substituted acetylene compound into a polysubstituted benzene compound or a polysubstituted pyridine compound. It is another object of the present invention to provide a process for addition reaction to produce polysubstituted benzene and polysubstituted pyridine through addition of an electrophilic reagent to the organotitanium compound.

In order to achieve the above-mentioned object, the present inventors carried out extensive studies, which led to the finding that it is possible to produce an organotitanium compound from a titanium reagent as a reaction product of a tetravalent titanium compound (which is commercially inexpensive) and a Grignard reagent, the organotitanium compound being capable of converting three molecules of acetylene compound, or one molecule of acetylene compound and one molecule of diyne compound, into a benzene compound regioselectively, or converting two molecules of acetylene compound and one molecule of nitrile compound into a pyridine compound regioselectively. The present invention is based on this finding.

The present invention provides the following.

[1] A process for producing an organotitanium compound which comprises reacting an acetylene compound represented by the formula (1) below in the presence of a titanium compound represented by the formula (2) below and a Grignard reagent represented by the formula (3) below with an acetylene compound represented by the formula (4) below and further reacting with a compound represented by the formula (5) below, thereby giving the titanium compound represented by the formula (6) and/or (7) below.

[where $R^1$ and $R^2$ denote mutually independently a $C_{1-20}$ alkyl group {which may be substituted with a $C_{1-6}$ alkoxy group (which may be substituted with a phenyl group) or $OSiR^7R^8R^9$ (where $R^7$, $R^8$, and $R^9$ denote mutually independently a $C_{1-6}$ alkyl group or phenyl group)}, $C_{3-20}$ alkenyl group, $C_{1-6}$ alkoxy group, $C_{1-6}$ alkoxycarbonyl group, $C_{1-6}$ alkylaminocarbonyl group, di-$C_{1-6}$-alkylaminocarbonyl group, phenyl group (which may be substituted with a $C_{1-6}$ alkyl group, $C_{1-6}$ alkoxy group, $C_{1-6}$ alkoxycarbonyl group, $C_{1-6}$ alkylaminocarbonyl group, or di-$C_{1-6}$-alkylaminocarbonyl group), furyl group, amino group, $SiR^7R^8R^9$ (where $R^7$, $R^8$, and $R^9$ denote mutually independently a $C_{1-6}$ alkyl group or phenyl group), or $SnR^{10}R^{11}R^{12}$ (where $R^{10}$, $R^{11}$, and $R^{12}$ denote mutually independently a halogen atom, $C_{1-6}$ alkyl group, or phenyl group).]

$$TiX^1X^2X^3X^4 \quad (2)$$

[where $X^1$, $X^2$, $X^3$, and $X^4$ denote mutually independently a halogen atom, $C_{1-6}$ alkoxy group {which may be substituted with a phenyl group (which may be substituted with a $C_{1-6}$ alkyl group, $C_{1-6}$ alkoxy group, or phenyl group) or naphthyl group}, phenoxy group (which may be substituted with a $C_{1-6}$ alkyl group, $C_{1-6}$ alkoxy group, or phenoxy group), or naphthoxy group.]

$$RMgX^5 \quad (3)$$

[where R denotes a $C_{2-8}$ alkyl group having a hydrogen atom at the β position, and $X^5$ denotes a halogen atom.]

[where $R^3$ and $R^4$ denote mutually independently a hydrogen atom, $C_{1-20}$ alkyl group, $C_{1-6}$ alkoxy group, $C_{1-6}$ alkoxycarbonyl group, $C_{1-6}$ alkylaminocarbonyl group, di-$C_{1-6}$-alkylaminocarbonyl group, phenyl group (which may be substituted with a $C_{1-6}$ alkyl group, $C_{1-6}$ alkoxy group, $C_{1-6}$ alkoxycarbonyl group, $C_{1-6}$ alkylaminocarbonyl group, or di-$C_{1-6}$-alkylaminocarbonyl group), furyl group, amino group, $SiR^7R^8R^9$ (where $R^7$, $R^8$, and $R^9$ are defined as above), or $SnR^{10}R^{11}R^{12}$ (where $R^{10}$, $R^{11}$, and $R^{12}$ are defined as above).]

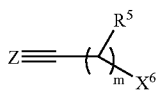

[where $R^5$ denotes a hydrogen atom, $C_{1-20}$ alkyl group, or phenyl group (which may be substituted with a $C_{1-6}$ alkyl group, $C_{1-6}$ alkoxy group, $C_{1-6}$ alkoxycarbonyl group, $C_{1-6}$ alkylaminocarbonyl group, or di-$C_{1-6}$-alkylaminocarbonyl group); Z denotes CR' (where R' denotes a hydrogen atom or $C_{1-20}$ alkyl group) or a nitrogen atom; $X^6$ denotes a halogen atom, $C_{1-6}$ alkoxy group {which may be substituted with a phenyl group (which may be substituted with a $C_{1-6}$ alkyl group, $C_{1-6}$ alkoxy group, or phenyl group) or naphthyl group}, phenoxy group (which may be substituted with a $C_{1-6}$ alkyl group, $C_{1-6}$ alkoxy group, or phenyl group), naphthoxy group, $SO_nR^6$ group {where $R^6$ denotes a $C_{1-6}$ alkyl group or phenyl group (which may be substituted with a halogen atom or $C_{1-6}$ alkyl group) and n denotes 1 or 2}, $OSO_2R^6$ group (where $R^6$ is defined as above), or $OP(O)(OR_{13})_2$ group (where $R^{13}$ denotes a $C_{1-6}$ alkyl group); and m denotes 0 or 1.]

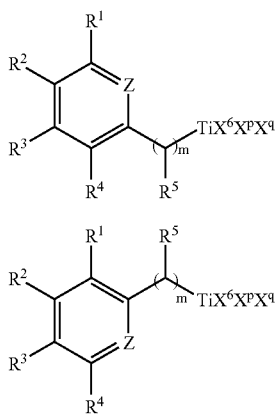

[where $R^1$~$R^5$, Z, $X^6$, and m are defined as above; and $X^p$ and $X^q$ denote any of $X^1$~$X^4$ (which are defined as above).]

[2] A process for producing an organotitanium compound which comprises reacting an acetylene compound represented by the formula (8) below in the presence of a titanium compound represented by the formula (2) below and a Grignard reagent represented by the formula (3) below with a compound represented by the formula (5) below, thereby giving the titanium compound represented by the formula (9) and/or (10) below.

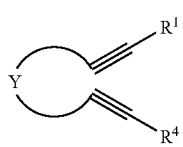

[where $R^1$ denotes a $C_{1-20}$ alkyl group {which may be substituted with a $C_{1-6}$ alkoxy group (which may be substituted with a phenyl group) or $OSiR^7R^8R^9$ (where $R^7$, $R^8$, and $R^9$ denote mutually independently a $C_{1-6}$ alkyl group or phenyl group)}, $C_{3-20}$ alkenyl group, $C_{1-6}$ alkoxy group, $C_{1-6}$ alkoxycarbonyl group, $C_{1-6}$ alkylaminocarbonyl group, di-$C_{1-6}$-alkylaminocarbonyl group, phenyl group (which may be substituted with a $C_{1-6}$ alkyl group, $C_{1-6}$ alkoxy group, $C_{1-6}$ alkoxycarbonyl group, $C_{1-6}$ alkylaminocarbonyl group, or di-$C_{1-6}$-alkylaminocarbonyl group), furyl group, amino group, $SiR^7R^8R^9$ (where $R^7$, $R^8$, and $R^9$ are defined as above), or $SnR^{10}R^{11}R^{12}$ (where $R^{10}$, $R^{11}$, and $R^{12}$ denote mutually independently a halogen atom, $C_{1-6}$ alkyl group, or phenyl group); $R^4$ denotes a hydrogen atom, $C_{1-20}$ alkyl group, $C_{1-6}$ alkoxy group, $C_{1-6}$ alkoxycarbonyl group, $C_{1-6}$ alkylaminocarbonyl group, di-$C_{1-6}$-alkylaminocarbonyl group, phenyl group (which may be substituted with a $C_{1-6}$ alkyl group, $C_{1-6}$ alkoxy group, $C_{1-6}$ alkoxycarbonyl group, $C_{1-6}$ alkylaminocarbonyl group, or di-$C_{1-6}$-alkylaminocarbonyl group), furyl group, amino group, $SiR^7R^8R^9$ (where $R^7$, $R^8$, and $R^9$ are defined as above), or $SnR^{10}R^{11}R^{12}$ (where $R^{10}$, $R^{11}$, and $R^{12}$ are defined as above); and Y denotes $Z^1$-$Z^2$-$Z^3$ or $Z^4$-$Z^5$-$Z^6$-$Z^7$ {where $Z^1$, $Z^3$, $Z^4$, $Z^5$, and $Z^7$ denote mutually independently C=O or $CR^{14}R^{15}$ <where $R^{14}$ and $R^{15}$ denote mutually independently a hydrogen atom or $C_{1-6}$ alkyl group (which may be substituted with a $C_{1-6}$ alkoxy group (which may be substituted with a phenyl group) or $OSiR^7R^8R^9$ (where $R^7$, $R^8$, and $R^9$ are defined as above))>, $Z^2$ and $Z^6$ denote mutually independently O, S, C=O, $NR^{16}$ <where $R^{16}$ denotes a $C_{1-6}$ alkyl group (which may be substituted with a $C_{1-6}$ alkoxy group (which may be substituted with a phenyl group) or $OSiR^7R^8R^9$ (where $R^7$, $R^8$, and $R^9$ are defined as above))>, or $CR^{14'}R^{15'}$ <where $R^{14'}$ and $R^{15'}$ denote mutually independently a hydrogen atom or $C_{1-6}$ alkyl group (which may be substituted with a $C_{1-6}$ alkoxy group (which may be substituted with a phenyl group) or $OSiR^7R^8R^9$ (where $R^7$, $R^8$, and $R^9$ are defined as above))>}.]

$$TiX^1X^2X^3X^4 \quad (2)$$

[where $X^1$, $X^2$, $X^3$, and $X^4$ denote mutually independently a halogen atom, $C_{1-6}$ alkoxy group {which may be substituted with a phenyl group (which may be substituted with a $C_{1-6}$ alkyl group, $C_{1-6}$ alkoxy group, or phenyl group), or a naphthyl group}, phenoxy group (which may be substituted with a $C_{1-6}$ alkyl group, $C_{1-6}$ alkoxy group, or phenyl group), or naphthoxy group.]

$$RMgX^5 \quad (3)$$

[where R denotes a $C_{2-8}$ alkyl group having a hydrogen atom at the β position, and $X^5$ denotes a halogen atom.]

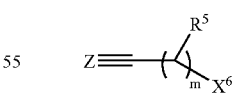

[where $R^5$ denotes a hydrogen atom, $C_{1-20}$ alkyl group, or phenyl group (which may be substituted with a $C_{1-6}$ alkyl group, $C_{1-6}$ alkoxy group, $C_{1-6}$ alkoxycarbonyl group, $C_{1-6}$ alkylaminocarbonyl group, or di-$C_{1-6}$-alkylaminocarbonyl group), Z denotes CR' (where R' denotes a hydrogen atom or $C_{1-20}$ alkyl group) or a nitrogen atom; $X^6$ denotes a halogen atom, $C_{1-6}$ alkoxy group {which may be substituted with a phenyl group (which may be substituted with a $C_{1-6}$ alkyl group, $C_{1-6}$ alkoxy group, or phenyl group), or naphthyl group}, phenoxy group (which may be substituted with a $C_{1-6}$ alkyl group, $C_{1-6}$ alkoxy group, or phenyl group), naphthoxy group, $SO_nR^6$ {where $R^6$ denotes a $C_{1-6}$ alkyl group or phenyl group (which may be substituted with a halogen atom or $C_{1-6}$ alkyl group) and n denotes 1 or 2}, $OSO_2R^6$ (where $R^6$ is defined as above), or $OP(O)(OR^{13})_2$ group (where $R^{13}$ denotes a $C_{1-6}$ alkyl group); and m denotes 0 or 1.]

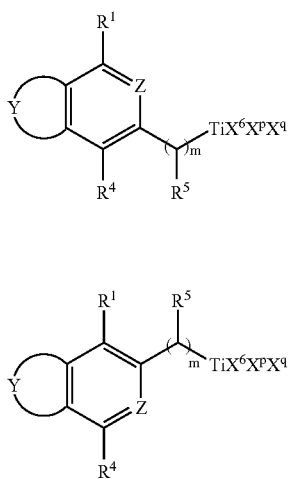

[where $R^1$, $R^4$, $R^5$, Y, Z, $X^6$, and m are defined as above; and $X^p$ and $X^q$ denote any of $X^1$~$X^4$ (which are defined as above).]

[3] A process for producing an organotitanium compound which comprises reacting an acetylene compound represented by the formula (1) below in the presence of a titanium compound represented by the formula (2) below and a Grignard reagent represented by the formula (3) below with a compound represented by the formula (11) below, thereby giving the titanium compound represented by the formula (12) below.

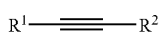

(1)

[where $R^1$ and $R^2$ denote mutually independently a $C_{1-20}$ alkyl group {which may be substituted with a $C_{1-6}$ alkoxy group (which may be substituted with a phenyl group) or $OSiR^7R^8R^9$ (where $R^7$, $R^8$, and $R^9$ denote mutually independently a $C_{1-6}$ alkyl group or phenyl group)}, $C_{3-20}$ alkenyl group, $C_{1-6}$ alkoxy group, $C_{1-6}$ alkoxycarbonyl group, $C_{1-6}$ alkylaminocarbonyl group, di-$C_{1-6}$-alkyaminocarbonyl group, phenyl group (which may be substituted with a $C_{1-6}$ alkyl group, $C_{1-6}$ alkoxy group, $C_{1-6}$ alkoxycarbonyl group, $C_{1-6}$ alkylaminocarbonyl group, or di-$C_{1-6}$-alkylaminocarbonyl group), furyl group, amino group, $SiR^7R^8R^9$ (where $R^7$, $R^8$, and $R^9$ are defined as above), or $SnR^{10}R^{11}R^{12}$ (where $R^{10}$, $R^{11}$, and $R^{12}$ denote mutually independently a halogen atom, $C_{1-6}$ alkyl group, or phenyl group).]

$TiX^1X^2X^3X^4$ (2)

[where $X^1$, $X^2$, $X^3$, and $X^4$ denote mutually independently a halogen atom, $C_{1-6}$ alkoxy group {which may be substituted with a phenyl group (which may be substituted with a $C_{1-6}$ alkyl group, $C_{1-6}$ alkoxy group, or phenyl group), or a naphthyl group}, phenoxy group (which may be substituted with a $C_{1-6}$ alkyl group, $C_{1-6}$ alkoxy group, or phenyl group), or naphthoxy group).]

$RMgX^5$ (3)

[where R denotes a $C_{2-8}$ alkyl group having a hydrogen atom at the β position, and $X^5$ denotes a halogen atom.]

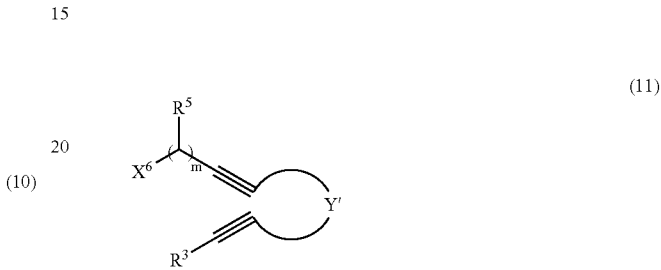

[where $R^3$ denotes a hydrogen atom, $C_{1-20}$ alkyl group, $C_{1-6}$ alkoxy group, $C_{1-6}$ alkoxycarbonyl group, $C_{1-6}$ alkylaminocarbonyl group, di-$C_{1-6}$-alkylaminocarbonyl group, phenyl group (which may be substituted with a $C_{1-6}$ alkyl group, $C_{1-6}$ alkoxy group, $C_{1-6}$ alkoxycarbonyl group, $C_{1-6}$ alkylaminocarbonyl group, or di-$C_{1-6}$-alkylaminocarbonyl group), furyl group, amino group, $SiR^7R^8R^9$ ($R^7$, $R^8$, and $R^9$ are defined as above), or $SnR^{10}R^{11}R^{12}$ (where $R^{10}$, $R^{11}$, and $R^{12}$ are defined as above); $R^5$ denotes a hydrogen atom, $C_{1-20}$ alkyl group, or phenyl group (which may be substituted with a $C_{1-6}$ alkyl group, $C_{1-6}$ alkoxy group, $C_{1-6}$ alkoxycarbonyl group, $C_{1-6}$ alkylaminocarbonyl group, or di-$C_{1-6}$-alkylaminocarbonyl group); Y' denotes $Z^1$-$Z^2$-$Z^3$ or $Z^4$-$Z^5$-$Z^6$-$Z^7$ {where $Z^1$, $Z^3$, $Z^4$, $Z^5$, and $Z^7$ denote mutually independently C=O or $CR^{14}R^{15}$ <where $R^{14}$ and $R^{15}$ denote mutually independently a hydrogen atom or $C_{1-6}$ alkyl group (which may be substituted with a $C_{1-6}$ alkoxy group (which may be substituted with a phenyl group) or $OSiR^7R^8R^9$ (where $R^7$, $R^8$, and $R^9$ are defined as above))>, $Z^2$ and $Z^6$ denote mutually independently O, S, C=O, $NR^{16}$ <where $R^{16}$ denotes a $C_{1-6}$ alkyl group (which may be substituted with $C_{1-6}$ alkoxy group (which may be substituted with a phenyl group)) or $OSiR^7R^8R^9$ (where $R^7$, $R^8$, and $R^9$ are defined as above)>, or $CR^{14'}R^{15'}$ <where $R^{14'}$ and $R^{15'}$ denote mutually independently a hydrogen atom, $C_{1-6}$ alkyl group (which may be substituted with a $C_{1-6}$ alkoxy group (which may be substituted with a phenyl group) or $OSiR^7R^8R^9$ (where $R^7$, $R^8$, and $R^9$ are defined as above))>}; $X^6$ denotes a halogen atom, $C_{1-6}$ alkoxy group {which may be substituted with a phenyl group (which may be substituted with a $C_{1-6}$ alkyl group, $C_{1-6}$ alkoxy group, or phenyl group), or naphthyl group}, phenoxy group (which may be substituted with a $C_{1-6}$ alkyl group, $C_{1-6}$ alkoxy group, or phenyl group), naphthoxy group, $SO_nR^6$ {where $R^6$ denotes a $C_{1-6}$ alkyl group or phenyl group (which may be substituted with a halogen atom or $C_{1-6}$ alkyl group), and n denotes 1 or 2}, OSO$_2$R$^6$ (where R$^6$ is defined as above), or OP(O)(OR$^{13}$)$_2$ group (where R$^{13}$ denotes a C$_{1-6}$ alkyl group); and m denotes 0 or 1.]

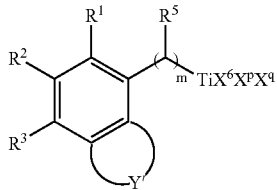

(12)

[where R$^1$ to R$^3$, R$^5$, Y', X$^6$, and m are defined as above; and X$^p$ and X$^q$ denote any of X$^1$~X$^4$ (which are defined as above).]

[4] A process for producing an organotitanium compound which comprises reacting an acetylene compound represented by the formula (1) below in the presence of a titanium compound represented by the formula (2) below and a Grignard reagent represented by the formula (3) below with a compound represented by the formula (13) below, thereby giving the titanium compound represented by the formula (14) below.

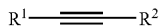

(1)

R$^1$══════R$^2$

[where R$^1$ and R$^2$ denote mutually independently a C$_{1-20}$ alkyl group {which may be substituted with a C$_{1-6}$ alkoxy group (which may be substituted with a phenyl group) or OSiR$^7$R$^8$R$^9$ (where R$^7$, R$^8$, and R$^9$ denote mutually independently a C$_{1-6}$ alkyl group or phenyl group)}, C$_{3-20}$ alkenyl group, C$_{1-6}$ alkoxy group, C$_{1-6}$ alkoxycarbonyl group, C$_{1-6}$ alkylaminocarbonyl group, di-C$_{1-6}$-alkyaminocarbonyl group, phenyl group (which may be substituted with a C$_{1-6}$ alkyl group, C$_{1-6}$ alkoxy group, C$_{1-6}$ alkoxycarbonyl group, C$_{1-6}$ alkylaminocarbonyl group, or di-C$_{1-6}$-alkylaminocarbonyl group), furyl group, amino group, SiR$^7$R$^8$R$^9$ (where R$^7$, R$^8$, and R$^9$ denote mutually independently a C$_{1-6}$ alkyl group or phenyl group), or SnR$^{10}$R$^{11}$R$^{12}$ (where R$^{10}$, R$^{11}$, and R$^{12}$ denote mutually independently a halogen atom, C$_{1-6}$ alkyl group, or phenyl group).]

TiX$^1$X$^2$X$^3$X$^4$ (2)

[where X$^1$, X$^2$, X$^3$, and X$^4$ denote mutually independently a halogen atom, C$_{1-6}$ alkoxy group {which may be substituted with a phenyl group (which may be substituted with a C$_{1-6}$ alkyl group, C$_{1-6}$ alkoxy group, or phenyl group) or naphthyl group}, phenoxy group (which may be substituted with a C$_{1-6}$ alkyl group, C$_{1-6}$ alkoxy group, or phenyl group), or naphthoxy group.]

RMgX$^5$ (3)

[where R denotes a C$_{2-8}$ alkyl group having a hydrogen atom at the β position, and X$^5$ denotes a halogen atom.]

(13)

R'══════X$^6$

[where R' denotes a hydrogen atom or C$_{1-20}$ alkyl group; and X$^6$ denotes a halogen atom, C$_{1-6}$ alkoxy group {which may be substituted with a phenyl group (which may be substituted with a C$_{1-6}$ alkyl group, C$_{1-6}$ alkoxy group, or phenyl group) or naphthyl group}, phenoxy group (which may be substituted with C$_{1-6}$ alkyl group, C$_{1-6}$ alkoxy group, or phenyl group), naphthoxy group, SO$_n$R$^6$ group (where R$^6$ denotes a C$_{1-6}$ alkyl group or phenyl group {which may be substituted with a halogen atom or C$_{1-6}$ alkyl group), and n denotes 1 or 2}, OSO$_2$R$^6$ (where R$^6$ is defined as above), or OP(O)(OR$^{13}$)$_2$ group (where R$^{13}$ denotes a C$_{1-6}$ alkyl group).]

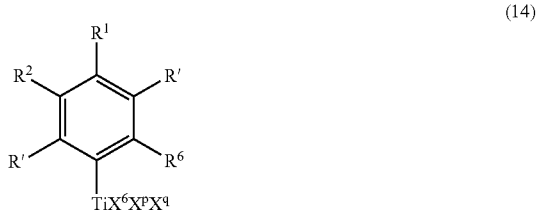

(14)

[where R$^1$, R$^2$, R', Z, and X$^6$ are defined as above; and X$^p$ and X$^q$ denote any of X$^1$ to X$^4$ (which are defined as above).]

[5] A process for producing an organotitanium compound as defined in any of [1] to [4] above, wherein the titanium compound is tetra-i-propoxytitanium.

[6] A process for producing an organotitanium compound as defined in any of [1] to [5] above, wherein the Grignard reagent is an i-propyl Grignard reagent.

[7] A process for addition reaction which comprises adding to the organotitanium compound obtained by the process defined in any of [1] to [6] above a compound having an electrophilic functional group or an electrophilic reagent, and performing addition reaction on the organotitanium compound.

[8] A process for addition reaction as defined in [7] above, wherein the electrophilic functional group is an aldehyde group, ketone group, imino group, hydrazone group, aliphatic double bond, aliphatic triple bond, acyl group, ester group, or carbonate group.

[9] A process for addition reaction as defined in [7] above, wherein the electrophilic reagent is water, heavy water, chlorine, bromine, iodine, N-bromosuccinimide, oxygen, carbon dioxide gas, or carbon monoxide.

DETAILED DESCRIPTION OF THE INVENTION

The invention will be described in more detail in the following. Incidentally, throughout this specification, "n" implies "normal", "i" implies "iso", "s" implies "secondary", "t" implies "tertiary", "c" implies "cyclo", "o" implies "ortho", "m" implies "meta", and "p" implies "para".

(A) Process For Producing Organotitanium Compound

In the acetylene compound represented by the formula (1), R$^1$ and R$^2$ denote mutually independently a C$_{1-20}$ alkyl group {which may be substituted with a C$_{1-6}$ alkoxy group (which may be substituted with a phenyl group) or OSiR$^7$R$^8$R$^9$ (where R$^7$, R$^8$, and R$^9$ denote mutually independently a C$_{1-6}$ alkyl group or phenyl group)}, C$_{3-20}$ alkenyl group, C$_{1-6}$ alkoxy group, C$_{1-6}$ alkoxycarbonyl group, C$_{1-6}$ alkylaminocarbonyl group, di-C$_{1-6}$-alkyaminocarbonyl group, phenyl group (which may be substituted with a C$_{1-6}$ alkyl group, C$_{1-6}$ alkoxy group, C$_{1-6}$ alkoxycarbonyl group, C$_{1-6}$ alkylaminocarbonyl group, or di-C$_{1-6}$-alkylaminocarbonyl group), furyl group, amino group, $SiR^7R^8R^9$ (where $R^7$, $R^8$, and $R^9$ denote mutually independently a $C_{1-6}$ alkyl group or phenyl group), or $SnR^{10}R^{11}R^{12}$ (where $R^{10}$, $R^{11}$, and $R^{12}$ denote mutually independently a halogen atom, $C_{1-6}$ alkyl group, or phenyl group).

The $C_{1-20}$ alkyl group may be a straight, branched, or cyclic one. It includes, for example, methyl, ethyl, n-propyl, i-propyl, n-butyl, i-butyl, s-butyl, t-butyl, n-pentyl, c-pentyl, n-hexyl, c-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl, and eicosanyl. It also includes those substituted alkyl groups, such as 2-methoxyethyl, 2-ethoxyethyl, 2-benzyloxyethyl, 2-trimethylsiloxyethyl, 2-t-butyldimethylsiloxyethyl, 2-t-butyldiphenylsiloxyethyl, 3-methoxypropyl, 3-ethoxypropyl, 3-benzyloxypropyl, 3-trimethylsiloxypropyl, 3-t-butyldimethylsiloxypropyl, 3-t-butyldiephenylsiloxypropyl, 4-methoxybutyl, 4-ethoxybutyl, 4-benzyloxybutyl, 4-trimethylsiloxybutyl, 4-t-butyldimethylsiloxybutyl, and 4-t-butyldiphenylsiloxybutyl.

Of these examples, favorable ones are methyl, ethyl, n-propyl, n-butyl, n-pentyl, n-hexyl, 2-methoxyethyl, 2-ethoxyethyl, 2-benzyloxyethyl, 2-trimethylsiloxyethyl, 2-t-butylmethylsiloxyethyl, and 2-t-butyldiphenylsiloxyethyl. Particularly favorable ones are methyl, n-butyl, n-hexyl, 2-bentyloxyethyl, and 2-t-butyldimethylsiloxyethyl.

The $C_{3-20}$ alkenyl group may be a straight, branched, or cyclic one. It includes, for example, allyl, 2-butenyl, 3-butenyl, 2-pentenyl, 3-pentenyl, 4-pentenyl, 2-hexenyl, 3-hexenyl, 4-hexenyl, 5-hexenyl, 6-heptenyl, 7-octenyl, 3,7-dimethyl-6-octenyl, 8-nonenyl, 9-decenyl, 10-undecenyl, 11-dodecenyl, 12-tridecenyl, 13-tetradecenyl, 14-pentadecenyl, 15-hexadecenyl, 16-heptadecenyl, 17-octadecenyl, 18-nonadecenyl, and 19-eicosenyl. Of these examples, 3,7-dimethyl-6-octenyl is favorable.

The $C_{1-6}$ alkoxy group may be a straight, branched, or cyclic one. It includes, for example, methoxy, ethoxy, n-propoxy, i-propoxy, c-propoxy, n-butoxy, i-butoxy, s-butoxy, t-butoxy, c-butoxy, 1-methyl-c-propoxy, 2-methyl-c-propoxy, pentoxy, c-pentoxy, hexoxy, and c-hexoxy. Of these examples, favorable ones are methoxy, ethoxy, n-butoxy, c-pentoxy, n-hexoxy, and c-hexoxy. c-Hexoxy is particularly favorable.

The $C_{1-6}$ alkoxycarbonyl group is not specifically restricted so long as it is a carbonyl group having the above-mentioned $C_{1-6}$ alkoxy group. It includes, for example, methoxycarbonyl, ethoxycarbonyl, n-propoxycarbonyl, i-propoxycarbonyl, n-butoxycarbonyl, i-butoxycarbonyl, t-butoxycarbonyl, t-amyloxycarbonyl, vinyloxycarbonyl, allyloxycarbonyl, 2-(trimethylsilyl)ethoxycarbonyl, 2,2,2-trichloroethoxycarbonyl, pentoxycarbonyl, and hexoxycarbonyl. Of these examples, favorable ones are methoxycarbonyl, ethoxycarbonyl, n-butoxycarbonyl, and t-butoxycarbonyl, and particularly favorable ones are ethoxycarbonyl and t-butoxycarbonyl.

The $C_{1-6}$ alkyl group may be a straight, branched, or cyclic one. It includes, for example, methyl, ethyl, n-propyl, i-propyl, c-propyl, n-butyl, i-butyl, s-butyl, t-butyl, c-butyl, 1-methyl-c-propyl, 2-methyl-c-propyl, n-pentyl, 1-methyl-n-butyl, 2-methyl-n-butyl, 3-methyl-n-butyl, 1,1-dimethyl-n-propyl, 1,2-dimethyl-n-propyl, 2,2-dimethyl-n-propyl, 1-ethyl-n-propyl, c-pentyl, 1-methyl-c-butyl, 2-methyl-c-butyl, 3-methyl-c-butyl, 1,2-dimethyl-c-propyl, 2,3-dimethyl-c-propyl, 1-ethyl-c-propyl, 2-ethyl-c-propyl, n-hexyl, 1-methyl-n-pentyl, 2-methyl-n-pentyl, 3-methyl-n-pentyl, 4-methyl-n-pentyl, 1,1-dimethyl-n-butyl, 1,2-dimethyl-n-butyl, 1,3-dimethyl-n-butyl, 2,2-dimethyl-n-butyl, 2,3-dimethyl-n-butyl, 3,3-dimethyl-n-butyl, 1-ethyl-n-butyl, 2-ethyl-n-butyl, 1,1,2-trimethyl-n-propyl, 1,2,2-trimethyl-n-propyl, 1-ethyl-1-methyl-n-propyl, 1-ethyl-2-methyl-n-propyl, c-hexyl, 1-methyl-c-pentyl, 2-methyl-c-pentyl, 3-methyl-c-pentyl, 1-ethyl-c-butyl, 2-ethyl-c-butyl, 3-ethyl-c-butyl, 1,2-dimethyl-c-butyl, 1,3-dimethy c-butyl, 2,2-dimethyl-c-butyl, 2,3-dimethyl-c-butyl, 2,4-dimethyl-c-butyl, 3,3-dimethyl-c-butyl, 1-n-propyl-c-propyl, 2-n-propyl-c-propyl, 1-i-propyl-c-propyl, 2-i-propyl-c-propyl, 1,2,2-trimethyl-c-propyl, 1,2,3-trimethyl-c-propyl, 2,2,3-trimethyl-c-propyl, 1-ethyl-2-methyl-c-propyl, 2-ethyl-1-methyl-c-propyl, 2-ethyl-2-methyl-c-propyl, and 2-ethyl-3-methyl-c-propyl.

The $C_{1-6}$ alkylaminocarbonyl group and di-$C_{1-6}$-alkylaminocarbonyl group are not specifically restricted so long as they are (di)alkylaminocarbonyl groups having the above-mentioned $C_{1-6}$ alkyl group on the nitrogen atom. They include, for example, (di)methylaminocarbonyl, (di)ethylaminocarbonyl, (di)propylaminocarbonyl, and (di)butylaminocarbonyl. Of these examples, favorable ones are (di)methylaminocarbonyl, (di)ethylaminocarbonyl, and (di) n-propylaminocarbonyl. Particularly favorable one is (di) ethylaminocarbonyl.

The phenyl group includes, for example, phenyl, o-methylphenyl, m-methylphenyl, p-methylphenyl, p-ethylphenyl, p-i-propylphenyl, p-t-butylphenyl, o-methoxyphenyl, p-methoxyphenyl, 3,5-dimethylphenyl, 3,5-dimethoxyphenyl, 3,5-diethylphenyl, 3,5-di-i-propylphenyl, 2,4,6-trimethylphenyl, and 2,4,6-trimethoxyphenyl. Of these examples, phenyl is favorable.

The $SiR^7R^8R^9$ group is not specifically restricted so long as its substituent groups (any of $R^7$, $R^8$, and $R^9$) are mutually independently a $C_{1-6}$ alkyl group or phenyl group. It includes, for example, trimethylsilyl, triethylsilyl, triisopropylsilyl, tributylsilyl, t-butyldimethylsilyl, t-butyldiphenylsilyl, diphenylmethylsilyl, and triphenylsilyl. Of these examples, favorable ones are trimethylsilyl, t-butyldimethylsilyl, and t-butyldiphenylsilyl. Particularly favorable ones are trimethylsilyl and t-butyldimethylsilyl.

The $SnR^{10}R^{11}R^{12}$ group is not specifically restricted so long as its substituent groups (any of $R^{10}$, $R^{11}$, and $R^{12}$) are mutually independently a halogen atom, $C_{1-6}$ alkyl group, or phenyl group. It includes, for example, trimethyltin, triethyltin, tributyltin, trichlorotin, and triphenyltin. Of these examples, favorable ones are trimethyltin, triphenyltin, and trichlorotin.

Incidentally, the halogen atom may be any of fluorine, chlorine, bromine, and iodine.

In the titanium compound represented by the formula (2) above, $X^1$, $X^2$, $X^3$, and $X^4$ denote mutually independently a halogen atom, $C_{1-6}$ alkoxy group {which may be substituted with a phenyl group (which may be substituted with a $C_{1-6}$ alkyl group, $C_{1-6}$ alkoxy group, or phenyl group) or naphthyl group}, phenoxy group (which may be substituted with a $C_{1-6}$ alkyl group, $C_{1-6}$ alkoxy group, or phenoxy group), or naphthoxy group.

The $C_{1-6}$ alkoxy group includes (in addition to the above-exemplified alkoxy groups) benzyloxy, o-methylbenzyloxy, m-methylbenzyloxy, p-methylbenzyloxy, o-methoxybenzyloxy, p-methoxybenzyloxy, phenethyloxy, o-methylphenethyloxy, m-methylphenethyloxy, p-methylphenethyloxy, o-methoxyphenethyloxy, p-methoxyphenethyloxy, 3-pheylpropoxy, 4-phenylbutoxy, 5-phenylpentoxy, 6-phenylhexoxy, a-naphthylmethoxy, β-naphthylmethoxy, o-biphenylylmethoxy, m-biphenylylmethoxy, p-biphenylylmethoxy, α-naphthylethoxy, β-naphthylethoxy, o-biphenylylethoxy, m-biphenylylethoxy, and p-biphenylylethoxy. Of these examples, favorable ones are methoxy, ethoxy, n-propoxy, i-propoxy, and n-butoxy.

The phenoxy group or naphthoxy group is not specifically restricted; it includes, for example, phenoxy, o-methylphenoxy, m-methylphenoxy, p-methylphenoxy, p-ethylphenoxy, p-i-propylphenoxy, p-t-butylphenoxy, o-methoxyphenoxy, p-methoxyphenoxy, α-naphthoxy, β-naphthoxy, o-biphenyloxy, m-biphenyloxy, and p-biphenyloxy.

The halogen atom X is not specifically restricted as mentioned above. A favorable halogen is chlorine.

Incidentally, the $C_{1-6}$ alkyl group is defined as above.

Typical examples of the titanium compound include tetra-i-propoxytitanium, chlorotri-i-propoxytitanium, and dichlorodi-i-propoxytitanium. Of these examples, tetra-i-propoxytitanium is favorable.

In the Grignard reagent represented by the formula (3) above, R denotes a $C_{2-8}$ alkyl group having a hydrogen atom at the β position, and $X^5$ denotes a halogen atom.

R (which is a $C_{2-8}$ alkyl group having a hydrogen atom at the β position) may be a straight, branched, or cyclic alkyl group which is not specifically restricted so long as it has a hydrogen atom at the β position. It includes, for example, ethyl, n-propyl, i-propyl, c-propyl, n-butyl, i-butyl, s-butyl, t-butyl, c-butyl, 1-methyl-c-propyl, 2-methyl-c-propyl, n-pentyl, 1-methyl-n-butyl, 2-methyl-n-butyl, 3-methyl-n-butyl, 1,1-dimethyl-n-propyl, 1,2-dimethyl-n-propyl, 1-ethyl-n-propyl, c-pentyl, 1-methyl-c-butyl, 2-methyl-c-butyl, 3-methyl-c-butyl, 1,2-dimethyl-c-propyl, 2,3-dimethyl-c-propyl, 1-ethyl-c-propyl, 2-ethyl-c-propyl, n-hexyl, 1-methyl-n-pentyl, 2-methyl-n-pentyl, 3-methyl-n-pentyl, 4-methyl-n-pentyl, 1,1-dimethyl-n-butyl, 1,2-dimethyl-n-butyl, 1,3-dimethyl-n-butyl, 2,3-dimethyl-n-butyl, 3,3-diemthyl-n-butyl, 1-ethyl-n-butyl, 2-ethyl-n-butyl, 1,1,2-trimethyl-n-propyl, 1-ethyl-1-methyl-n-propyl, 1-ethyl-2-methyl-n-propyl, c-hexyl, 1-methyl-c-pentyl, 2-methyl-c-pentyl, 3-methyl-c-pentyl, 1-ethyl-c-butyl, 2-ethyl-c-butyl, 3-ethyl-c-butyl, 1,2-dimethyl-c-butyl, 1,3-dimethyl-c-butyl, 2,2-dimethyl-c-butyl, 2,3-dimethyl-c-butyl, 2,4-dimethyl-c-butyl, 3,3-dimethyl-c-butyl, 1-n-propyl-c-propyl, 2-n-propyl-c-propyl, 1-i-propyl-c-propyl, 2-i-propyl-c-propyl, 1,2,2-trimethyl-c-propyl, 1,2,3-trimethyl-c-propyl, 2,2,3-trimethyl-c-propyl, 1-ethyl-2-methyl-c-propyl, 2-ethyl-1-methyl-c-propyl, 2-ethyl-2-methyl-c-propyl, 2-ethyl-3-methyl-c-propyl, n-heptyl, 5-methyl-n-hexyl, c-heptyl, n-octyl, 6-methyl-n-heptyl, and c-octyl. Of these examples, favorable ones are ethyl, n-propyl, i-propyl, n-butyl, and i-butyl.

The halogen atom ($X^5$) is not specifically restricted. Favorable ones are chlorine and bromine.

Typical examples of the Grignard reagent include ethyl Grignard reagent (such as ethyl magnesium chloride and ethyl magnesium bromide), n-propyl Grignard reagent (such as n-propyl magnesium chloride and n-propyl magnesium bromide), and i-propyl Grignard reagent (such as i-propyl magnesium chloride and i-propyl magnesium bromide). Of these examples, a favorable one is i-propyl Grignard reagent.

In the acetylene compound represented by the formula (4) above, $R^3$ and $R^4$ denote mutually independently a hydrogen atom, $C_{1-20}$ alkyl group, $C_{1-6}$ alkoxy group, $C_{1-6}$ alkoxycarbonyl group, $C_{1-6}$ alkylaminocarbonyl group, di-$C_{1-6}$-alkylaminocarbonyl group, phenyl group (which may be substituted with a $C_{1-6}$ alkyl group, $C_{1-6}$ alkoxy group, $C_{1-6}$ alkoxycarbonyl group, $C_{1-6}$ alkylaminocarbonyl group, or di-$C_{1-6}$-alkylaminocarbonyl group), furyl group, amino group, $SiR^7R^8R^9$ (where $R^7$, $R^8$, and $R^9$ are defined as above), or $SnR^{10}R^{11}R^{12}$ (where $R^{10}$, $R^{11}$, and $R^{12}$ are defined as above).

The $C_{1-20}$ alkyl group, $C_{1-6}$ alkoxy group, $C_{1-6}$ alkoxycarbonyl group, $C_{1-6}$ alkylaminocarbonyl group, di-$C_{1-6}$-alkylaminocarbonyl group, $SiR^7R^8R^9$ group, and $SnR^{10}R^{11}R^{12}$ group are the same as those defined in the acetylene compound represented by the formula (1) above.

In the compound represented by the formula (5) above, $R^5$ denotes a hydrogen atom, $C_{1-20}$ alkyl group, or phenyl group (which may be substituted with a $C_{1-6}$ alkyl group, $C_{1-6}$ alkoxy group, $C_{1-6}$ alkoxycarbonyl group, $C_{1-6}$ alkylaminocarbonyl group, or di-$C_{1-6}$-alkylaminocarbonyl group); Z denotes CR' (where R' denotes a hydrogen atom or $C_{1-20}$ alkyl group) or a nitrogen atom; $X^6$ denotes a halogen atom, $C_{1-6}$ alkoxy group {which may be substituted with a phenyl group (which may be substituted with a $C_{1-6}$ alkyl group, $C_{1-6}$ alkoxy group, or phenyl group) or naphthyl group}, phenoxy group (which may be substituted with a $C_{1-6}$ alkyl group, $C_{1-6}$ alkoxy group, or phenyl group), naphthoxy group, $SO_nR^6$ group {where $R^6$ denotes a $C_{1-6}$ alkyl group or phenyl group (which may be substituted with a halogen atom or $C_{1-6}$ alkyl group) and n denotes 1 or 2}, $OSO_2R^6$ group (where $R^6$ is defined as above), or $OP(O)(OR^{13})_2$ group (where $R^{13}$ denotes a $C_{1-6}$ alkyl group); and m denotes 0 or 1.

The $SO_nR^6$ group is not specifically restricted; it includes, for example, methanesulfinyl, p-toluenesulfinyl, p-trifluoromethanesulfinyl, methanesulfonyl, benzenesuflonyl, p-toluenesulfonyl, and p-trifluoromethanesulfonyl. Of these examples, favorable ones are p-toluenesulfonyl and p-toluenesulfinyl.

The $OSO_2R^6$ group is not specifically restricted; it includes, for example, methanesulfonyloxy, benzenesufonyloxy, p-toluenesulfonyloxy, and p-trifluoromethanesulfonyloxy groups. Of these examples, a favorable one is p-toluenesulfonyloxy group.

The $OP(O)(OR^{13})_2$ group is not specifically restricted; it includes, for example, dimethyl phosphate, diethyl phosphate, and diphenyl phosphate. Of these example, a favorable one is diethyl phosphate.

Incidentally, the $C_{1-20}$ alkyl group, phenyl group, $C_{1-6}$ alkoxycarbonyl group, $C_{1-6}$ alkylaminocarbonyl group, di-$C_{1-6}$-alkylaminocarbonyl group, halogen atom, $C_{1-6}$ alkoxy group, phenoxy group, and naphthoxy group are the same as those defined above.

In the diyne compound in the formula (8) above, the terminal substituent groups $R^1$ and $R^4$ are also defined as above.

Y denotes $Z^1$-$Z^2$-$Z^3$ or $Z^4$-$Z^5$-$Z^6$-$Z^7$ {where $Z^1$, $Z^3$, $Z^4$, $Z^5$, and $Z^7$ denote mutually independently C=O or $CR^{14}R^{15}$ <where $R^{14}$ and $R^{15}$ denote mutually independently a hydrogen atom or $C_{1-6}$ alkyl group (which may be substituted with a $C_{1-6}$ alkoxy group (which may be substituted with a phenyl group) or $OSiR^7R^8R^9$ (where $R^7$, $R^8$, and $R^9$ are defined as above))>, $Z^2$ and $Z^6$ denote mutually independently O, S, C=O, $NR^{16}$ <where $R^{16}$ denotes a $C_{1-6}$ alkyl group (which may be substituted with a $C_{1-6}$ alkoxy group (which may be substituted with a phenyl group) or $OSiR^7R^8R^9$ (where $R^7$, $R^8$, and $R^9$ are defined as above))>, or $CR^{14'}R^{15'}$ <where $R^{14'}$ and $R^{15'}$ denote mutually independently a hydrogen atom, $C_{1-6}$ alkyl group (which may be substituted with a $C_{1-6}$ alkoxy group (which may be substituted with a phenyl group) or $OSiR^7R^8R^9$ (where $R^7$, $R^8$, and $R^9$ are defined as above))>}.

Y is not specifically restricted; it includes, for example, $(CH_2)_3$, $(CH_2)_4$, $CH_2C(CH_2OCH_2Ph)_2CH_2$, $CH_2C$ $(CH_2OSiMe_3)_2CH_2$, $CH_2C(CH_2OSit\text{-}BuMe_2)_2CH_2$, $CH_2C(CH_2OCH_3)_2CH_2$, $CH_2OCH_2$, $CH_2SCH_2$, $CH_2C(O)CH_2$, $C(O)N(CH_2Ph)CH_2$, $C(O)N(CH_3)CH_2$, $C(O)N(CH_2Ph)C(O)$, and $C(O)N(CH_3)C(O)$. Of these examples, favorable ones are $(CH_2)_3$, $CH_2C(CH_2OCH_2Ph)_2CH_2$, and $C(O)N(CH_2Ph)CH_2$. Me stands for a methyl group, Ph stands for a phenyl group, and t-Bu stands for a t-butyl group.

In the compound represented by the formula (11) or (13), $R^3$, $R^5$, R', and $X^6$ are defined as above. Y' is the same as Y mentioned above.

A mention is given below of the process for producing the organotitanium compound represented by the formula (6) and/or (7).

The process consists of reacting an acetylene compound represented by the formula (1) in the presence of a titanium compound represented by the formula (2) and a Grignard reagent represented by the formula (3) with a compound represented by the formula (4) and further reacting with a compound represented by the formula (5), thereby giving the titanium compound represented by the formula (6) and/or (7) above.

The molar amount of the titanium compound used in this reaction should be 0.01–5 times, preferably 0.5–2 times, the amount of the acetylene compound (as the substrate) represented by the formula (1). The molar amount of the Grignard reagent should be 1–10 times the amount of the titanium compound used. The amount should be limited to 1.5–2.5 times in order to avoid side reactions with the substrate.

The reaction may be carried out by adding the reactants in any order. One procedure involves mixing the titanium compound and the Grignard reagent and then adding to the mixture the acetylene compound (as the substrate) represented by the formula (1). Another procedure involves adding the titanium compound to the acetylene compound represented by the formula (1), and then adding the Grignard reagent. Either procedure will do.

The molar amount of the compound represented by the formula (4) should be 0.5–2 times, preferably 0.6–1.2 times, the amount of the acetylene compound represented by the formula (1).

The molar amount of the compound represented by the formula (5) should be 0.5–2 times, preferably 0.8–1.5 times, the amount of the acetylene compound represented by the formula (1).

The solvent used in the reaction is not specifically restricted so long as it is not involved in the reaction. It includes, for example, aromatic hydrocarbons (such as benzene, toluene, xylene, mesitylene, chlorobenzene, and o-dichlorobenzene), aliphatic hydrocarbons (such as n-hexane, cyclohexane, n-octane, and n-decane), halogenated hydrocarbons (such as dichloromethane, dichloroethane, chloroform, and carbon tetrachloride), and ethers (such as tetrahydrofuran, diethyl ether, t-butyl methyl ether, and dimethoxyethane). Of these examples, favorable ones are dichloromethane, tetrahydrofuran, and diethyl ether. They may be used alone or in combination with one another.

The reaction temperature is not specifically restricted; it may range from –100° C. to the boiling point of the solvent. Preferred reaction temperatures are within the range from –80° C. to 40° C. The reaction time is usually 0.1 to 1000 hours.

The above-mentioned reaction gives rise to the organotitanium compound represented by the above-mentioned formula (6) and/or (7). This compound is unstable out of the reaction system. Therefore, it is not isolated as such. Instead, the reaction system is given an electrophilic reagent to bring about addition reaction at the titanium bonding position, and the resulting addition product is isolated afterwards.

After the reaction is complete, the reaction system is given an aqueous solution of alkali to produce an aromatic compound in which a hydrogen atom is added to the titanium bonding position. Subsequently, this aromatic compound is extracted with an adequate solvent, and there is obtained a crude product upon condensation under reduced pressure. If necessary, the crude product is purified in the usual way by distillation, recrystallization, silica gel column chromatography, or the like. In this way it is possible to isolate the addition product in pure form.

It is presumed that the organotitanium compound represented by the formula (6) or (7) is formed by the following reaction mechanism.

The titanium compound and the Grignard reagent give rise to a divalent titanium complex, which reacts with the first acetylene compound represented by the formula (1) to give a titanacyclopropene intermediate. This intermediate reacts with the second acetylene compound represented by the formula (4) to give a titanacyclopendadiene intermediate. Between this intermediate and the compound represented by the formula (5) occurs cyclic addition reaction. This addition reaction eliminates the leaving group, thereby giving rise to the organotitanium compound represented by the formula (6) or (7).

It is presumed that the ratio in which the above-mentioned organotitanium compound is formed (or the orientation of the cyclic addition reaction) varies depending mainly on the electron-attracting property of the substituent group at the 1- and 4-position of the cyclopentadiene intermediate.

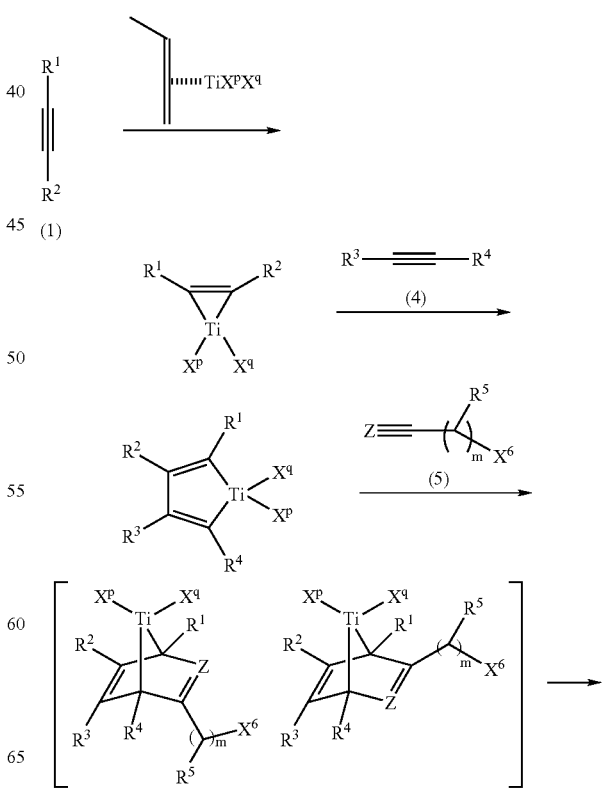

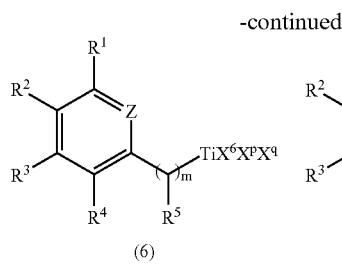

(6)          (7)

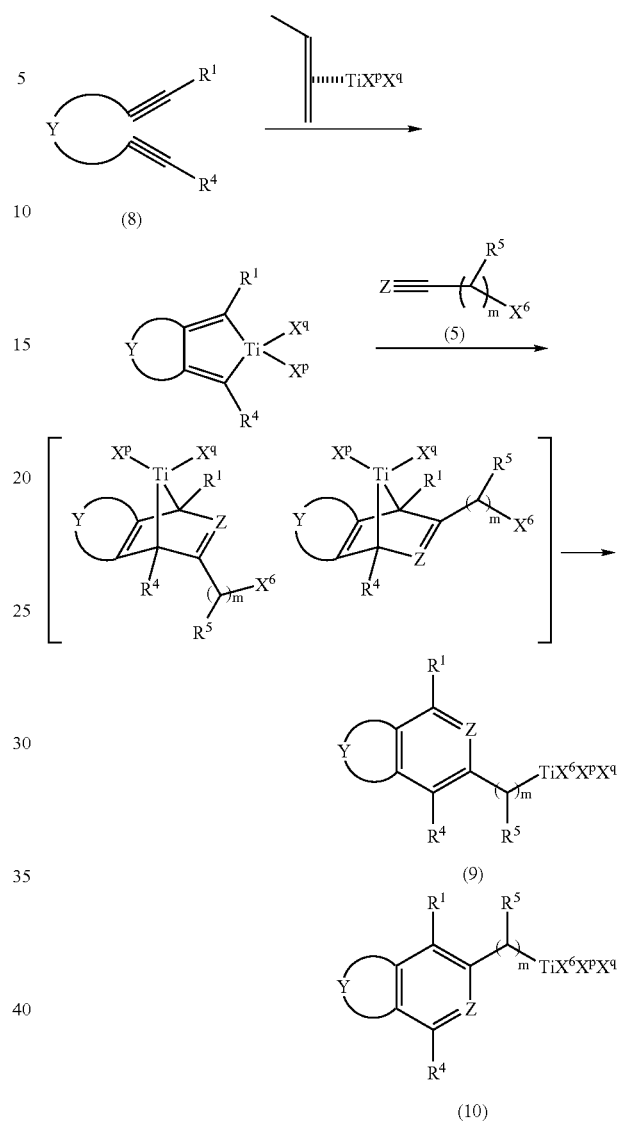

A mention is made below of the process for producing the organotitanium compound represented by the formulas (9) and/or (10) above.

The diyne compound represented by the formula (8) is reacted with the compound represented by the formula (4) above in the presence of the titanium compound represented by the formula (2) above and the Grignard reagent represented by the formula (3) above. The resulting reaction product is further reacted with the compound represented by the formula (5) to give the organotitanium compound represented by the formulas (9) and/or (10) above.

The molar amount of the titanium compound used in this reaction is 0.01–5 times, preferably 0.5–2 times, the amount of the diyne compound (as the substrate) represented by the formula (8). The molar amount of the Grignard reagent should be 1–10 times the amount of the titanium compound used. The amount should be limited to 1.5–2.5 times in order to avoid side reactions with the substrate.

The reaction may be carried out by adding the reactants in any order. One procedure involves mixing the titanium compound and the Grignard reagent and then adding to the mixture the diyne compound (as the substrate) represented by the formula (8). Another procedure involves adding the titanium compound to the diyne compound represented by the formula (8), and then adding the Grignard reagent. Either procedure will do.

The molar amount of the compound represented by the formula (5) should be 0.5–2 times, preferably 0.8–1.5 times, the amount of the diyne compound represented by the formula (8).

The solvent used in the reaction is not specifically restricted so long as it is not involved in the reaction. It includes those which have been listed above.

The reaction temperature is not specifically restricted; it may range from −100° C. to the boiling point of the solvent. Preferred reaction temperatures are within the range from −80° C. to 40° C. The reaction time is usually 0.1 to 1000 hours.

The above-mentioned reaction gives rise to the organotitanium compound represented by the above-mentioned formula (9) and/or (10). This compound is unstable out of the reaction system. Therefore, it is not isolated as such. Instead, the reaction system is given an electrophilic reagent to bring about addition reaction at the titanium bonding position, and the resulting addition product is isolated afterwards.

It is presumed that the organotitanium compound represented by the formula (9) or (10) is formed by the following reaction mechanism. The reaction mechanism is identical with that mentioned above, except that two molecules of the acetylene compounds represented by the formulas (1) and (4) are replaced by the diyne compound represented by the formula (8).

A mention is made below of the process for producing the organotitanium compound represented by the formulas (12) above.

The diyne compound represented by the formula (11) is reacted with the acetylene compound represented by the formula (1) above in the presence of the titanium compound represented by the formula (2) above and the Grignard reagent represented by the formula (3) above. In this way it is possible to produce the organotitanium compound represented by the formula (12) above.

The molar amount of the titanium compound used in this reaction is 0.01–5 times, preferably 0.5–2 times, the amount of the acetylene compound (as the substrate) represented by the formula (1). The molar amount of the Grignard reagent should be 1–10 times the amount of the titanium compound used. The amount should be limited to 1.5–2.5 times in order to avoid side reactions with the substrate.

The reaction may be carried out by adding the reactants in any order. One procedure involves mixing the titanium compound and the Grignard reagent and then adding to the mixture the acetylene compound (as the substrate) represented by the formula (1). Another procedure involves adding the titanium compound to the acetylene compound represented by the formula (1), and then adding the Grignard reagent. Either procedure will do.

The molar amount of the diyne compound represented by the formula (11) is 0.5–2 times, preferably 0.8–1.5 times, the amount of the acetylene compound represented by the formula (1).

The solvent used in the reaction is not specifically restricted so long as it is not involved in the reaction. It includes those which have been listed above.

The reaction temperature is not specifically restricted; it may range from −100° C. to the boiling point of the solvent. Preferred reaction temperatures are within the range from −80° C. to 40° C. The reaction time is usually 0.1 to 1000 hours.

The above-mentioned reaction gives rise to the organotitanium compound represented by the above-mentioned formula (12). This compound is unstable out of the reaction system. Therefore, it is not isolated as such. Instead, the reaction system is given an electrophilic reagent to bring about addition reaction at the titanium bonding position, and the resulting addition product is isolated afterwards.

It is presumed that the organotitanium compound represented by the formula (12) is formed by the following reaction mechanism. The reaction mechanism is identical with that mentioned above, except that two molecules of the acetylene compounds represented by the formulas (4) and (5) are replaced by the diyne compound represented by the formula (11). The reaction product has such a structure that the titanacyclopentadiene intermediate is connected to the acetylene compound as the third component. This determines the orientation of the cyclic addition and gives rise to a single organotitanium compound.

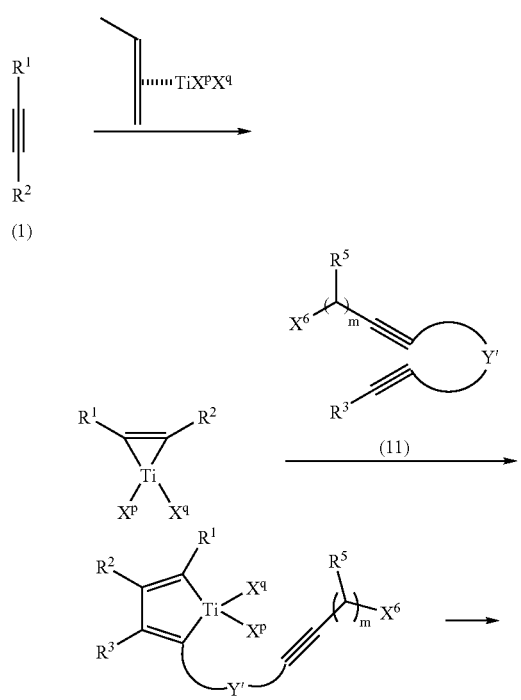

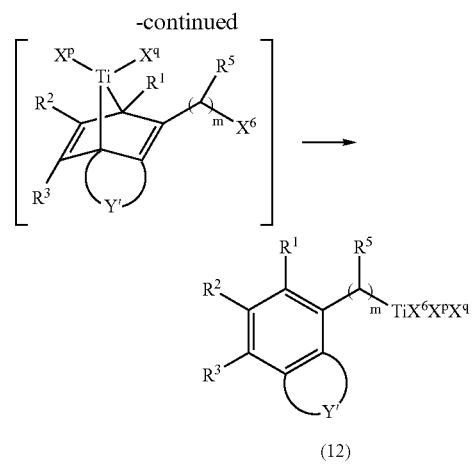

A mention is made below of the process for producing the organotitanium compound represented by the formulas (14) above.

The acetylene compound represented by the formula (1) is reacted with two molecules of the acetylene compound represented by the formula (13) above in the presence of the titanium compound represented by the formula (2) above and the Grignard reagent represented by the formula (3) above. In this way it is possible to produce the organotitanium compound represented by the formula (14) above.

The molar amount of the titanium compound used in this reaction is 0.01–5 times, preferably 0.5–2 times, the amount of the acetylene compound (as the substrate) represented by the formula (1). The molar amount of the Grignard reagent should be 1–10 times the amount of the titanium compound used. The amount should be limited to 1.5–2.5 times in order to avoid side reactions with the substrate.

The reaction may be carried out by adding the reactants in any order. One procedure involves mixing the titanium compound and the Grignard reagent and then adding to the mixture the acetylene compound (as the substrate) represented by the formula (1). Another procedure involves adding the titanium compound to the acetylene compound represented by the formula (1), and then adding the Grignard reagent. Either procedure will do.

The molar amount of the acetylene compound represented by the formula (13) is 1–4 times, preferably 1.6–3 times, the amount of the acetylene compound represented by the formula (1).

The solvent used in the reaction is not specifically restricted so long as it is not involved in the reaction. It includes those which have been listed above.

The reaction temperature is not specifically restricted; it may range from −100° C. to the boiling point of the solvent. Preferred reaction temperatures are within the range from −80° C. to 40° C. The reaction time is usually 0.1 to 1000 hours.

The above-mentioned reaction gives rise to the organotitanium compound represented by the above-mentioned formula (14). This compound is unstable out of the reaction system. Therefore, it is not isolated as such. Instead, the reaction system is given an electrophilic reagent to bring about addition reaction at the titanium bonding position, and the resulting addition product is isolated afterwards.

It is presumed that the organotitanium compound represented by the formula (14) is formed by the following reaction mechanism.

The titanium compound and the Grignard reagent give rise to a divalent titanium complex, which reacts with two molecules of the compounds having a triple bond to give a titanacyclopentadiene intermediate. This intermediate reacts with one molecule of the compound represented by the formula (13) for cyclic addition reaction. This addition reaction brings about transfer of titanium-carbon bond and eliminates the leaving group, thereby giving rise to the organotitanium compound represented by the formula (14).

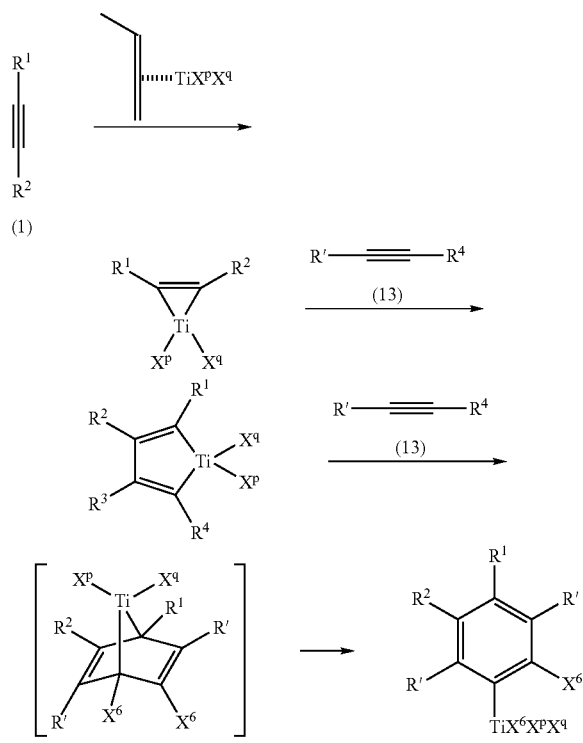

(B) Process For Addition Reaction

According to the present invention, the process for addition reaction consists of adding to the organotitanium compound obtained by the above-mentioned process a compound having an electrophilic functional group or an electrophilic reagent, and performing addition reaction on the organotitanium compound.

The electrophilic functional group is not specifically restricted so long as it reacts with the organotitanium compound of the present invention. It is preferably aldehyde group, ketone group, imino group, hydrazone group, aliphatic double bond, aliphatic triple bond, acyl group, ester group, or carbonate group. The compound having an electrophilic functional group includes, for example, aldehyde compound, ketone compound, imine compound, hydrazone compound, olefin compound, acetylene compound, acyl compound, ester compound, α,β-unsaturated carbonyl compound, and carbonate ester compound.

The aldehyde compound is not specifically restricted. It includes, for example, $C_{1-10}$ alkyl aldehyde, $C_{4-6}$ cycloalkyl aldehyde, $C_{3-14}$ cycloalkenyl aldehyde, benzaldehyde, o-halogenobenzaldehyde, m-halogenobenzaldehyde, p-halogenobenzaldehyde, $C_{1-10}$ alkyl ester-substituted phenyl aldehyde, o-halogenosuccin aldehyde, m-halogenosuccin aldehyde, p-halogenosuccin aldehyde, furylaldehyde, and thiophen aldehyde.

The ketone compound includes, for example, $C_{3-20}$ alkyl ketone, $C_{4-30}$ alkyl ester-substituted alkyl ketone, $C_{3-10}$ cycloalkyl ketone, acetophenone, tetralone, decalone, furyl ketone, and thiophenoketone. The imine compound includes, for example, the reaction product of the above-mentioned aldehyde compound with $C_{1-10}$ alkylamine, aniline, or benzylamine.

The hydrazone compound includes, for example, the reaction product of the above-mentioned ketone compound with $C_{1-10}$ alkyl hydrazine.

The olefin compound includes, for example, allyl alcohol derivatives which may have a substituent group. The allyl alcohol derivative includes, for example, $C_{4-13}$ allyl alcohol alkyl ester and $C_{4-13}$ allyl alcohol alkyl carbamate.

The allyl alcohol derivative may have a substituent group such as $C_{1-20}$ alkyl group, phenyl group, o-halogenophenyl group, m-halogenophenyl group, and p-halogenophenyl group.

The acetylene compound includes, for example, propargyl alcohol derivative which may have a substituent group and propargyl halide which may have a substituent group. The propargyl alcohol derivative includes, for example, $C_{4-13}$ propargyl alcohol alkyl ester, $C_{4-13}$ propargyl alcohol alkyl carbamate, $C_{4-13}$ propargyl alcohol alkyl ether, $C_{4-13}$ propargyl alcohol alkylsulfonic ester, propargyl alcohol-o-hydroxyphenylsulfonic ester, propargyl alcohol-m-hydroxyphenylsulfonic ester, propargyl alcohol-p-hydroxyphenylsulfonic ester, and $C_{4-13}$ propargyl alcohol alkyl phosphoric ester.

The propargyl halide includes, for example, propargyl chloride and propargyl bromide.

These propargyl alcohol derivatives and propargyl halides may have a substituent group such as $C_{1-20}$ alkyl group, phenyl group, o-halogenophenyl group, m-halogenophenyl group, p-halogenophenyl group, and trialkylsilyl group.

The electrophilic reagent is not specifically restricted so long as it reacts with the organotitanium compound of the present invention. It is preferably water, heavy water, chlorine, bromine, iodine, N-bromosuccinimide, oxygen, carbon dioxide gas, or carbon monoxide.

To be concrete, the process consists of adding to the organotitanium compound (prepared as mentioned above) the compound having an electrophilic functional group or the electrophilic reagent (which are collectively referred to as an electrophilic compound hereinafter), thereby causing addition reaction with the electrophilic compound to take place at the titanium bonding position.

The molar amount of the electrophilic compound should be 1–10 times, preferably 1–5 times, particularly 1–2 times, the amount of the organotitanium compound.

The reaction may be carried out by adding the electrophilic compound in any order. One procedure involves adding the electrophilic compound directly to the reaction system in which the organotitanium compound has been prepared. Another procedure involves adding a solution of the organotitanium compound to a solution in which the electrophilic compound has been dissolved. Either procedure will do.

The solvent used in the reaction is not specifically restricted so long as it is not involved in the reaction. It includes those which have been used for the production of the organotitanium compound.

The reaction temperature is not specifically restricted; it may range from −100° C. to the boiling point of the solvent.

Preferred reaction temperatures are within the range from −80° C. to 40° C. The reaction time is usually 0.1 to 1000 hours.

After the reaction is complete, the addition reaction product is extracted with an adequate solvent, and there is obtained a crude product upon condensation under reduced pressure. If necessary, the crude product is purified in the usual way by distillation, recrystallization, silica gel column chromatography, or the like. In this way it is possible to isolate the desired product in pure form.

EXAMPLES

The invention will be described in more detail with reference to the following examples, which are not intended to restrict the scope thereof.

In the structural formulas given below, Me denotes methyl group, Et denotes ethyl group, Bn denotes benzyl group, t-Bu denotes t-butyl group, Ph denotes phenyl group, Tol denotes p-tolyl group, and TBS denotes t-butyldimethylsilyl group.

Example 1

3-(t-butoxycarbonyl)-4-hexylphenyl p-tolylsulfone

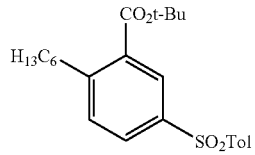

To a diethyl ether solution (7 mL) containing t-butyl 2-nonynoate (100 mg, 0.475 mmol) and tetra-i-propoxytitanium (0.175 mL, 0.594 mmol) was added i-propylmagnesium chloride (1.48 M diethyl ether solution, 0.900 mL, 1.33 mmol) at −78° C. under an argon stream. There was obtained a homogenous yellowish solution. The solution was slowly heated to −50° C. over 30 minutes. The solution turned into reddish. The solution was kept stirred for 5 hours at −50° C. The solution kept at −50° C. was given a diethyl ether solution (2 mL) containing powdery p-toluenesulfonylacetylene (171 mg, 0.951 mmol). Stirring was continued for 1 hour.

The reaction solution at room temperature was stirred for 3 hours and then given hydrochloric acid (1 mol/L) to suspend the reaction. The reaction product was extracted with diethyl ether.

The organic layer was washed with an aqueous solution of sodium bicarbonate and then dried with anhydrous sodium sulfate. The solvent was distilled away under reduced pressure. There was obtained a crude product in the form of oily substance. The crude product was analyzed in detail by $^1$H NMR. It was found to contain no other isomers. The crude product was purified by silica gel column chromatography (n-hexane-ethyl acetate). There was obtained 3-(t-butoxycarbonyl)-4-hexylphenyl p-tolylsulfone (98 mg, 50%) in the form of colorless oily substance.

$^1$H NMR: δ 0.84 (t, J=6.6 Hz, 3H, Me), 1.12–1.40 (m, 6H, alkyl H), 1.45–1.65 (m, 2H, alkyl H), 1.58 (s, 9H, C(CH$_3$)$_3$), 2.37 (s, 3H, PhMe), 2.90 (t, J=7.8 Hz, 2H, PhCH$_2$), 7.28 (d, J=8.4 Hz, 2H, Ph-H), 7.32 (d, J=8.1 Hz, 1H, Ph-H), 7.81 (d, J=8.4 Hz, 2H, Ph-H), 7.86 (dd, J=2.1, 8.1 Hz, 1H, Ph-H), 8.23 (d, J=2.1 Hz, 1H, Ph-H).

The structure was confirmed (identified) by the fact that a 12% increase in NOE (nuclear Overhauser effect) due to proton at δ 2.90 ppm (PhCH$_2$) was observed in the peak at δ 7.32 ppm (Ph-H).

$^{13}$C NMR: δ 13.84, 21.37, 22.35, 27.95 (C(CH$_3$)$_3$), 29.18, 31.39, 31.49, 34.21, 82.30 (CO$_2$C), 127.74 (o- or m-Ph), 129.26 (Ph), 129.47 (Ph), 129.98 (o- or m-Ph), 131.73 (Ph), 133.18 (Ph), 138.53 (Ph), 139.48 (Ph), 144.30 (Ph), 149.06 (Ph), 165.05 (C=O).

IR (neat): 3070 (Ph), 2960, 2927, 2860, 1715 (C=O), 1597, 1457, 1369 (S=O), 1256, 1156 (S=O), 914, 846, 813 cm$^{-1}$.

Elemental analysis: calculated (C$_{24}$H$_{32}$O$_4$S): C, 69.20%; H, 7.74%. found: C, 69.16%; H, 7.62%.

Example 2

3,4-dibutylphenyl p-tolylsulfone

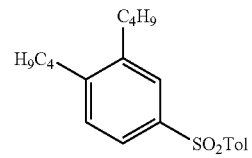

To a diethyl ether solution (1.5 mL) containing 5-decyne (0.020 mL, 0.111 mmol) and tetra-i-propoxytitanium (0.041 mL, 0.139 mmol) was added i-propylmagnesium chloride (1.63 M diethyl ether solution, 0.192 mL, 0.312 mmol) at −78° C. under an argon stream. There was obtained a homogenous yellowish solution. The solution was slowly heated to −50° C. over 30 minutes. The solution turned into blackish. The solution was kept stirred for 2 hours at −50° C. The solution (kept at −50° C.) was given a diethyl ether solution (1 mL) containing powdery p-toluenesulfonylacetylene (40 mg, 0.223 mmol). Stirring was continued for 1 hour.

The reaction solution at room temperature was stirred for 3 hours and then given hydrochloric acid (1 mol/L) to suspend the reaction. The reaction product was extracted with diethyl ether.

The organic layer was washed with an aqueous solution of sodium bicarbonate and then dried with anhydrous sodium sulfate. The solvent was distilled away under reduced pressure. There was obtained a crude product in the form of oily substance. The crude product was analyzed in detail by $^1$H NMR. It was found that it contained no other isomers. The crude product was purified by silica gel column chromatography (n-hexane-ethyl acetate). There was obtained 3,4-dibutylphenyl p-tolylsulfone (25 mg, 65%) in the form of colorless oily substance.

$^1$H NMR: δ 0.92 (t, J=7.5 Hz, 3H, Me), 0.94 (t, J=7.5 Hz, 3H, Me), 1.38 (sextet, J=7.5 Hz, 4H, alkyl H), 1.52 (quintet, J=7.5 Hz, 4H, alkyl H), 2.39 (s, 3H, PhMe), 2.61 (t, J=7.5 Hz, 2H, PhMe), 2.62 (t, J=7.5 Hz, 2H, PhCH$_2$), 7.23 (d, J=8.1 Hz, 1H, Ph-H), 7.28 (d, J=8.4 Hz, 2H, Ph-H), 7.63 (dd, J=2.1, 8.1 Hz, 1H, Ph-H), 7.70 (d, J =2.1 Hz, 1H, Ph-H), 7.82 (d, J=8.4 Hz, 2H, Ph-H).

$^{13}$C NMR: δ 13.78 (2 peaks), 21.42, 22.58 (2 peaks), 32.21, 32.26, 32.87, 32.89, 124.97 (Ph), 127.63 (o- or m-Ph), 127.96 (Ph), 129.87 (o- or m-Ph), 130.01 (Ph), 139.05 (Ph), 139.32 (Ph), 142.09 (Ph), 143.86 (Ph), 146.64 (Ph).

IR (neat): 3060 (Ph), 3020 (Ph), 2957, 2929, 2870, 1597, 1465, 1402, 1379, 1320 (S=O), 1301, 1179, 1154 (S=O), 1107, 1085, 911, 812, 733, 708, 683 cm$^{-1}$.

Elemental analysis: calculated ($C_{21}H_{28}O_2S$): C, 73.21%; H, 8.19%. found: C, 73.04%; H, 8.07%.

Example 3

5-(t-butoxycarbonyl)-2-deuterio-4-hexylphenyl p-tolylsulfone

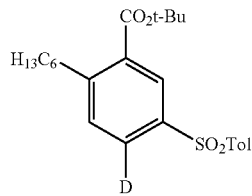

The same procedure as in Example 1 was repeated except that heavy water was added for reaction before the addition of hydrochloric acid (1 mol/L). There was obtained 5-(t-butoxycarbonyl)-2-deuterio-4-hexylphenyl p-tolylsulfone.

$^1$H NMR: δ 0.84 (t, J=6.6 Hz, 3H, Me), 1.12–1.40 (m, 6H, alkyl H), 1.45–1.65 (m, 2H, alkyl H), 1.58 (s, 9H, C(CH$_3$)$_3$), 2.37 (s, 3H, PhMe), 2.90 (t, J=7.8 Hz, 2H, PhCH$_2$), 7.28 (d, J=8.4 Hz, 2H, Ph-H), 7.32 (s, 1H, Ph-H), 7.81 (d, J=8.4 Hz, 2H, Ph-H), 8.23 (s, 1H, Ph-H).

An introduction of 78% deuterium was indicated by the degree of disappearance of the proton peak corresponding to δ 7.86 (Ph-H) of 3-(t-butoxycarbonyl)-4-hexylphenyl p-tolylsulfone.

Example 4

4,5-dibutyl-2-deuteriophenyl p-tolylsulfone

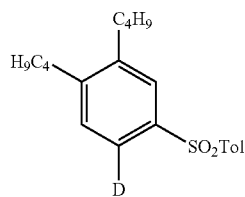

The same procedure as in Example 2 was repeated except that heavy water was added for reaction before the addition of hydrochloric acid (1 mol/L). There was obtained 4,5-dibutyl-2-deuteriophenyl p-tolylsulfone.

$^1$H NMR: δ 0.92 (t, J=7.5 Hz, 3H, Me), 0.94 (t, J=7.5 Hz, 3H, Me), 1.38 (sextet, J=7.5 Hz, 4H, alkyl H), 1.52 (quintet, J=7.5 Hz, 4H, alkyl H), 2.39 (s, 3H, PhMe), 2.61 (t, J=7.5 Hz, 2H, PhCH$_2$), 2.62 (t, J=7.5 Hz, 2H, PhCH$_2$), 7.23 (s, 1H, Ph-H), 7.28 (d, J=8.4 Hz, 2H, Ph-H), 7.70 (s, 1H, Ph-H), 7.82 (d, J=8.4 Hz, 2H, Ph-H).

An introduction of 80% deuterium was indicated by the degree of disappearance of the proton peak corresponding to δ 7.63 (Ph-H) of 3,4-dibutylphenyl p-tolylsulfone.

Example 5 t-butyl 2,4-dihexylbenzoate

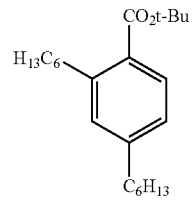

To a diethyl ether solution (1.5 mL) containing t-butyl 2-nonynoate (20 mg, 0.095 mmol) and tetra-i-propoxytitanium (0.035 mL, 0.119 mmol) was added i-propylmagnesium chloride (1.63 M diethyl ether solution, 0.163 mL, 0.266 mmol) at −78° C. under an argon stream. There was obtained a homogenous yellowish solution. The solution was slowly heated to −50° C. over 30 minutes. The solution turned into reddish. The solution was kept stirred for 5 hours at −50° C. The solution (kept at −50° C.) was given 1-octyne (0.011 mL, 0.076 mmol), and the solution was stirred for 3 hours. The solution was given a diethyl ether solution (1 mL) containing powdery p-toluenesulfonylacetylene (21 mg, 0.114 mmol). The reaction solution was heated to room temperature.

The reaction solution (at room temperature) was stirred for 3 hours and then given hydrochloric acid (1 mol/L) to suspend the reaction. The reaction product was extracted with diethyl ether. The organic layer was washed with an aqueous solution of sodium bicarbonate and then dried with anhydrous sodium sulfate. The solvent was distilled away under reduced pressure. There was obtained a crude product in the form of oily substance. The crude product was analyzed in detail by $^1$H NMR. It was found to contain no other isomers. The crude product was purified by silica gel column chromatography (n-hexane-diethyl ether). There was obtained t-butyl 2,4-dihexylbenzoate (15 mg, 57%) in the form of colorless oily substance.

$^1$H NMR: δ 0.87, (t, J=7.5 Hz, 6H, Me), 1.20–1.42 (m, 16H, alkyl H), 1.58 (s, 9H, C(CH$_3$)$_3$), 2.58 (t, J=7.8 Hz, 2H, PhCH$_2$), 2.89 (t, J=7.8 Hz, 2H, PhCH$_2$), 7.00 (s, 1H, Ph-H), 7.01 (d, J=8.4 Hz, 1H, Ph-H), 7.67 (d, J=8.4 Hz, 1H, Ph-H).

The structure was confirmed (identified) by the fact that a 5% increase in NOE due to irradiate proton at δ 2.58 ppm (PhCH$_2$) was observed in both the peak at δ 7.00 ppm (Ph-H) and the peak at δ 7.01 ppm (Ph-H) and the fact that a 9% increase in NOE due to proton at δ 2.89 ppm (PhCH$_2$) was observed in the peak at δ 7.00 ppm (Ph-H).

$^{13}$C NMR: δ 13.96 (2 peaks), 22.49, 22.53, 28.15 (C(CH$_3$)$_3$), 28.87, 29.38, 31.08, 31.60, 31.74, 31.89, 34.44, 35.71, 80.76 (CO$_2$C), 125.73 (Ph), 129.25 (Ph), 130.54 (Ph), 130.96 (Ph), 143.81 (Ph), 146.49 (Ph), 167.80 (C=O), IR (neat): 3010 (Ph), 2957, 2928, 2857, 1716 (C=O), 1609, 1458, 1366, 1275, 1258, 1180, 1142, 1100, 1071, 1100, 1070 cm$^{-1}$.

Elemental analysis: calculated ($C_{23}H_{38}O_2$): C, 79.71%; H, 11.05%. found: C, 79.57%; H, 10.84%.

The synthesized sample was found identical with the reference material of t-butyl 2,4-dihexylbenzoate which was synthesized separately from commercial 4-bromoisophthalic acid in the following manner.

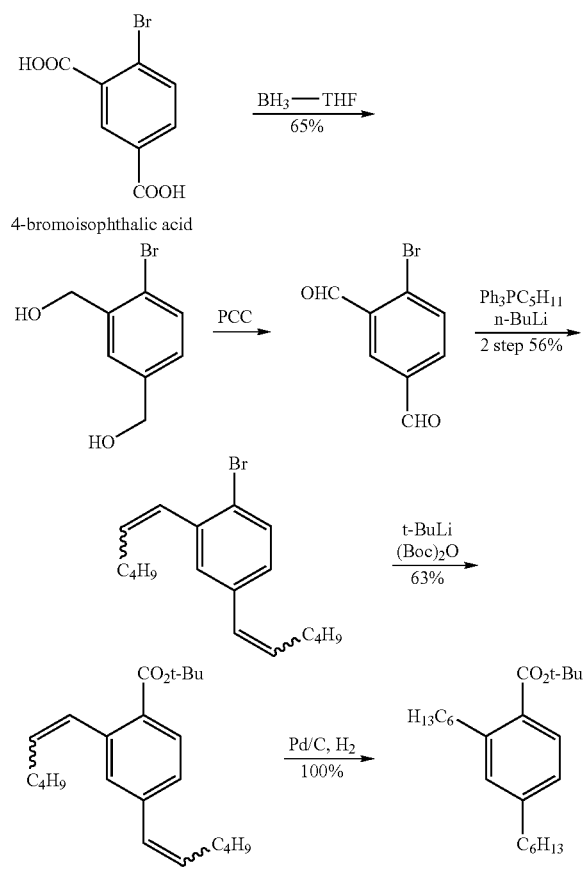

Example 6 t-butyl 2,4-dihexylbenzoate

The same procedure as in Example 5 was repeated except that p-toluenesulfonylacetylene was replaced by p-toluenesulfinylacetylene. There was obtained t-butyl 2,4-dihexylbenzoate in a 17% yield.

Example 7 t-butyl 2-deuterio-4,6-dihexylbenzoate

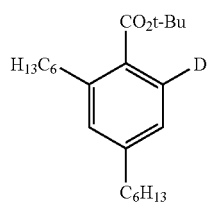

The same procedure as in Example 5 was repeated except that heavy water was added for reaction before the addition of hydrochloric acid (1 mol/L). There was obtained t-butyl 2-deuterio-4, 6-dihexylbenzoate.

$^1$H NMR: δ 0.87 (t, J=7.5 Hz, 6H, Me), 1.20–1.42 (m, 16H, alkyl H), 1.58 (s, 9H, C(CH$_3$)$_3$), 2.58 (t, J=7.8 Hz, 2H, PhCH$_2$), 2.89 (t, J=7.8 Hz, 2H, PhCH$_2$), 7.01 (s, 2H, Ph-H).

An introduction of 98% deuterium was indicated by the degree of disappearance of the proton peak corresponding to δ 7.67 (Ph-H) of t-butyl 2,4-dihexylbenzoate.

Example 8 t-butyl 2,4-dihexyl-6-iodobenzoate

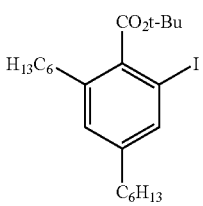

To a diethyl ether solution (1.5 mL) containing t-butyl 2-nonynoate (20 mg, 0.095 mmol) and tetra-i-propoxytitanium (0.035 mL, 0.119 mmol) was added i-propylmagnesium chloride (1.63 M diethyl ether solution, 0.163 mL, 0.266 mmol) at −78° C. under an argon stream. There was obtained a homogenous yellowish solution. The solution was slowly heated to −50° C. over 30 minutes. The solution turned into reddish. The solution was kept stirred for 5 hours at −50° C. The solution kept at −50° C. was given 1-octyne (0.011 mL, 0.076 mmol), and the solution was stirred for 3 hours. The solution was given a diethyl ether solution (1 mL) containing powdery p-toluenesulfonylacetylene (21 mg, 0.114 mmol). The reaction solution was heated to room temperature.

The reaction solution was stirred at room temperature for 3 hours and then given a tetrahydrofuran solution (1 mL) containing iodine (72 mg, 0.285 mmol). The solution was stirred for 1 hour and then given hydrochloric acid (1 mol/L) to suspend the reaction. The reaction product was extracted with diethyl ether. The organic layer was washed with an aqueous solution of sodium bicarbonate and sodium thiosulfate and then dried with anhydrous sodium sulfate. The solvent was distilled away under reduced pressure. There was obtained a crude product in the form of oily substance. The crude product was analyzed in detail by $^1$H NMR. It was found to contain no other isomers. The crude product was purified by silica gel column chromatography (n-hexane-diethyl ether). There was obtained t-butyl 2,4-dihexyl-6-iodobenzoate (20 mg, 56%) in the form of colorless oily substance.

$^1$H NMR: δ 0.80–0.95 (m, 6H, Me), 1.12–1.45 (m, 16H, alkyl H), 1.62 (s, 9H, C(CH$_3$)$_3$), 2.50 (t, J=7.8 Hz, 2H, PhCH$_2$), 2.57 (t, J=7.8 Hz, 2H, PhCH$_2$), 6.95 (d, J=1.5 Hz, 1H, Ph-H), 7.46 (d, J=1.5 Hz, 1H, Ph-H).

$^{13}$C NMR: δ 13.93 (2 peaks), 22.45 (2 peaks), 28.01 (C(CH$_3$)$_3$), 28.76, 29.22, 31.01, 31.37, 31.53, 31.57, 34.18, 35.14, 82,71 (CO$_2$C), 91.96 (Ph), 129.22 (Ph), 136.47 (Ph), 138.16 (Ph), 140.91 (Ph), 145.46 (Ph), 168.52 (C=O).

IR (neat): 3010 (Ph), 2960, 2927, 2857, 1725 (C=O), 1600, 1546, 1458, 1391, 1367, 1285, 1260, 1146, 1101, 1070, 847 cm$^{-1}$.

Example 9

5,7-dihexyl-3-phenylphthalide

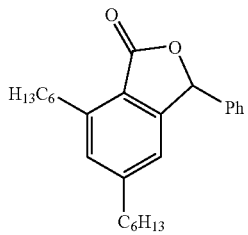

To a diethyl ether solution (1.5 mL) containing t-butyl 2-nonynoate (30 mg, 0.143 mmol) and tetra-i-propoxytitanium (0.053 mL, 0.178 mmol) was added i-propylmagnesium chloride (1.35 M diethyl ether solution, 0.296 mL, 0.399 mmol) at −78° C. under an argon stream. There was obtained a homogenous yellowish solution. The solution was slowly heated to −50° C. over 30 minutes. The solution turned into reddish. The solution was kept stirred for 5 hours at −50° C. The solution kept at −50° C. was given 1-octyne (0.017 mL, 0.114 mmol), and the solution was stirred for 3 hours. The solution was given a diethyl ether solution (1 mL) containing powdery p-toluenesulfonylacetylene (31 mg, 0.171 mmol). The reaction solution was heated to room temperature. The reaction solution was stirred at room temperature for 3 hours and then cooled to −50° C. The solution was given benzaldehyde (0.899 M, diethyl ether solution, 0.190 mL, 0.171 mmol). The solution was stirred at −50° C. for 2 hours and then heated to room temperature. Stirring was continued at room temperature for 5 hours.

The solution was given hydrochloric acid (1 mol/L) to suspend the reaction. The reaction product was extracted with diethyl ether. The organic layer was washed with an aqueous solution of sodium bicarbonate and then dried with anhydrous sodium sulfate. The solvent was distilled away under reduced pressure. There was obtained a crude product in the form of oily substance. The crude product was analyzed in detail by $^1$H NMR. It was found to contain no other isomers. The crude product was purified by silica gel column chromatography (n-hexane-diethyl ether). There was obtained 5,7-dihexyl-3-phenylphthalide (21 mg, 49%) in the form of colorless oily substance.

$^1$H NMR: δ 0.80–0.95 (m, 6H, Me), 1.20–1.50 (m, 12H, alkyl H), 1.50–1.76 (m, 4H, alkyl H), 2.62 (t, J=7.8 Hz, 2H, PhCH$_2$), 3.06 (dt, J=2.1, 7.8 Hz, 1H, PhCH$_2$), 3.13 (dt, J=2.1, 7.8 H, 1H, PhCH$_2$), 6.27 (s, 1H, CO$_2$CH), 6.90 (s, 1H, Ph-H), 7.11 (s, 1H, Ph-H), 7.25–7.31 (m, 2H, Ph-H), 7.34–7.42 (m, 3H, Ph-H).

The structure was confirmed (identified) by the fact that a 9% increase in NOE due to irradiate proton at δ 2.62 ppm (PhCH$_2$) was observed in both the peak at δ 6.90 ppm (Ph-H) and the peak at δ 7.11 ppm (Ph-H) and the fact that a 9% increase in NOE due to irradiate proton at δ 3.06 ppm (PhCH$_2$) and proton at δ 3.13 ppm (PhCH$_2$) was observed in the peak at δ 7.00 ppm (Ph-H).

$^{13}$C NMR: δ 13.88, 13.95, 22.41, 22.49, 28.81, 29.04, 30.89, 30.92, 31.06, 31.47, 31.59, 36.18, 81.53 (CO$_2$C), 119.95 (Ph), 120.32 (Ph), 127.10 (o- or m-Ph), 128.93 (m- or o-Ph), 129.10 (Ph), 130.52 (Ph), 137.29 (Ph), 144.63 (Ph), 150.32 (Ph), 151.03 (Ph), 170.54 (C=O).

IR (neat): 3070 (Ph), 3038 (Ph), 2960, 2860, 1761 (C=O), 1610, 1458, 1301, 1204, 1056, 698 cm$^{-1}$.

Example 10 t-butyl 2-hexyl-4-(trimethylsilyl)benzoate

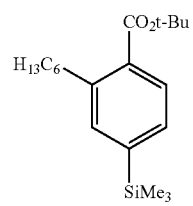

The same procedure as in Example 5 was repeated except that 1-octyne was replaced by trimethylsilylacetylene. There was obtained t-butyl 2-hexyl-4-(trimethylsilyl)benzoate in a 46% yield.

$^1$H NMR: δ 0.27 (s, 9H, SiMe$_3$), 0.88, (t, J=7.5 Hz, 3H, Me), 1.15–1.45 (m, 8H, alkyl H), 1.59 (s, 9H, C(CH$_3$)$_3$), 2.90 (t, J=7.8 Hz, 2H, PhCH$_2$), 7.33 (s, 1H, Ph-H), 7.36 (d, J=7.5 Hz, 1H, Ph-H), 7.69 (d, J=7.5 Hz, 1H, Ph-H).

$^{13}$C NMR: δ −1.43 (SiMe$_3$), 13.96, 22.55, 28.12 (C(CH$_3$)$_3$), 29.42, 31.71, 32.02, 34.43, 81.05 (CO$_2$C), 129.13 (Ph), 130.61 (Ph), 132.43 (Ph), 135.80 (Ph), 142.20 (Ph), 144.37 (Ph), 167.99 (C=O).

IR (neat): 3005 (Ph), 2957, 2925, 2860, 1717 (C=O), 1458, 1367, 1250 (SiMe$_3$), 1150, 840 cm$^{-1}$.

Elemental analysis: calculated (C$_{20}$H$_{34}$O$_2$Si): C, 71.80%; H, 10.24%. found: C, 71.64%; H, 10.53%.

Example 11 t-butyl 2-deuterio-6-hexyl-4-(trimethylsilyl)benzoate

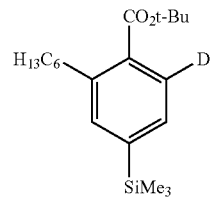

The same procedure as in Example 10 was repeated except that heavy water was added for reaction before the addition of hydrochloric acid (1 mol/L). There was obtained t-butyl 2-deuterio-6-hexyl-4-(trimethylsilyl)benzoate.

$^1$H NMR: δ 0.27 (s, 9H, SiMe$_3$), 0.88 (t, J=7.5 Hz, 3H, Me), 1.15–1.45 (m, 8H, alkyl H), 1.59 (s, 9H, C(CH$_3$)$_3$), 2.90 (t, J=7.8 Hz, 2H, PhCH$_2$), 7.33 (s, 1H, Ph-H), 7.36 (s, 1H, Ph-H).

An introduction of 94% deuterium was indicated by the degree of disappearance of the proton peak corresponding to δ 7.69 (Ph-H) of t-butyl 2-hexyl-4-trimethylsilyl)benzoate.

Example 12

4-[2-(benzyloxy)ethyl]-1,2-dibutylbenzene

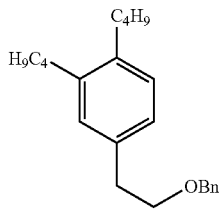

To a diethyl ether solution (1.5 mL) containing 5-decyne (0.02 mL, 0.111 mmol) and tetra-i-propoxytitanium (0.041 mL, 0.139 mmol) was added i-propyl-magnesium chloride (1.63 M diethyl ether solution, 0.192 mL, 0.312 mmol) at −78° C. under an argon stream. There was obtained a homogenous yellowish solution. The solution was slowly heated to −50° C. over 30 minutes. The solution turned into blackish. The solution was kept stirred for 2 hours at −50° C. The solution kept at −50° C. was given a diethyl ether solution (1 mL) containing 4-benzyloxy-1-butyne (14 mg, 0.089 mmol) and then stirred for 1 hour. The solution was given a diethyl ether solution (1 mL) containing powdery p-toluenesulfonylacetylene (22 mg, 0.122 mmol). The reaction solution was heated to room temperature.

The reaction solution at room temperature was stirred for 3 hours and then given hydrochloric acid (1 mol/L) to suspend the reaction. The reaction product was extracted with diethyl ether. The organic layer was washed with an aqueous solution of sodium bicarbonate and then dried with anhydrous sodium sulfate. The solvent was distilled away under reduced pressure. There was obtained a crude product in the form of oily substance. The crude product was analyzed in detail by $^1$H NMR. It was found to contain no other isomers. The crude product was purified by silica gel column chromatography (n-hexane-diethyl ether). There was obtained 4-[2-(benzyloxy)ethyl]-1,2-dibutylbenzene (17 mg, 57%) in the form of colorless oily substance.

$^1$H NMR: δ 0.95 (t, J=7.5 Hz, 6H, Me), 1.40 (sextet, J=7.5 Hz, 4H, alkyl H), 1.52 (quintet, J=7.5 Hz, 4H, alkyl H), 2.58 (t, J=7.5 Hz, 4H, PhCH$_2$), 2.89 (t, J=7.5 Hz, 2H, PhCH$_2$), 3.68 (t, J=7.5 Hz, 2H, CH$_2$OBn), 4.54 (s, 2H, PhCH$_2$O), 6.98 (d, J=7.5 Hz, 1H, Ph-H), 7.00 (s, 1H, Ph-H), 7.06 (d, J=7.5 Hz, 1H, Ph-H), 7.25–7.40 (m, 5H, Ph-H).

$^{13}$C NMR: δ 13.91 (2 peaks), 22.73, 22.80, 31.93, 32.34, 33.46, 33.49, 35.89, 71.48 (O—C), 72.91 (O—C), 126.29 (Ph), 127.57 (Ph), 127.71 (o- or m-Ph), 128.41 (m- or o-Ph), 129.19 (Ph), 129.85 (Ph), 136.12 (Ph), 138.47 (Ph), 138.60 (Ph), 140.60 (Ph).

IR (neat): 3090 (Ph), 3070 (Ph), 3035 (Ph), 3000 (Ph), 2955 (Ph), 2928, 2859, 1497, 1456, 1362, 1205, 1102, 1029, 822, 734, 696 cm$^{-1}$.

Elemental analysis: calculated (C$_{23}$H$_{32}$O): C, 85.13%; H, 9.94%. found: C, 85.38%; H, 10.03%.

Example 13

A 72:28 mixture of 1-[2-(benzyloxy)ethyl]-4,5-dibutyl-2-iodobenzene and 5-[2-(benzyloxy)ethyl]-1,2-dibutyl-3-iodobenzene.

The same procedure as in Example 12 was repeated except that iodine was added for reaction before the addition of hydrochloric acid (1 mol/L). There was obtained a 72:28 mixture of 1-[2-(benzyloxy)ethyl]-4,5-dibutyl-2-iodobenzene and 5-[2-(benzyloxy)ethyl]-1,2-dibutyl-3-iodobenzene in a 39% yield.

1-[2-(benzyloxy)ethyl]-4,5-dibutyl-2-iodobenzene

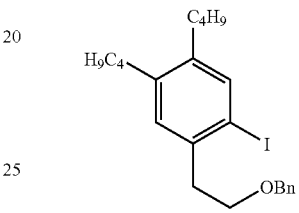

(Analyzed from a 72:28 mixture of position isomers.)

$^1$H NMR: δ 0.80–1.04 (m, 6H, Me), 1.20–1.60 (m, 8H, alkyl H), 2.51 (t, J=7.7 Hz, 4H, PhCH$_2$), 3.00 (t, J=7.5 Hz, 2H, PhCH$_2$), 3.66 (t, J=7.5 Hz, 2H, CH$_2$OBn), 4.55 (s, 2H, PhCH$_2$O), 7.03 (s, 1H, Ph-H), 7.25–7.40 (m, 5H, Ph-H), 7.56 (s, 1H, Ph-H).

The structure was confirmed (identified) by the fact that a 9% increase and a 13% increase in NOE due to irradiate proton at δ 2.51 ppm (PhCH$_2$) were observed respectively in the peaks at δ 7.03 ppm (Ph-H) and δ 7.56 ppm (Ph-H) and the fact that a 14% increase in NOE due to irradiate proton at δ 3.00 ppm (PhCH$_2$) was observed in the peak at δ 7.03 ppm (Ph-H).

IR (neat): 3090 (Ph), 3060 (Ph), 3035 (Ph), 2955, 2928, 2859, 1456, 1380, 1362, 1205, 1102, 1030, 733, 696 cm$^{-1}$.

5-[2-(benzyloxy)ethyl]-1,2-dibutyl-3-iodobenzene

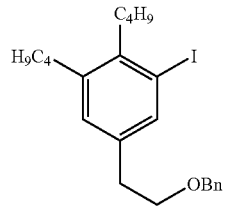

$^1$H NMR: (characteristic peaks only) δ 2.80 (t, J=7.5 Hz, 2H, PhCH$_2$), 3.65 (t, J=7.5 Hz, 2H, CH$_2$OBn), 4.52 (s, 2H, PhCH$_2$O), 6.96 (s, 1H, Ph-H), 7.56 (s, 1H, Ph-H).

Example 14

4-[2-((t-butyl)dimethylsiloxy)ethyl]-2-hexyl-1-(trimethylsilyl) benzene

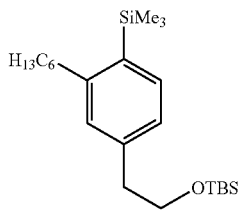

To a diethyl ether solution (4.5 mL) containing 1-trimethylsilyl-1-octyne (60 mg, 0.329 mmol) and tetra-i-propoxytitanium (0.121 mL, 0.411 mmol) was added i-propylmagnesium chloride (1.46 M diethyl ether solution, 0.630 mL, 0.921 mmol) at −78° C. under an argon stream. There was obtained a homogenous yellowish solution. The solution was slowly heated to −50° C. over 30 minutes. The solution turned into blackish. The solution was kept stirred for 2 hours at −50° C. The solution kept at −50° C. was given a diethyl ether solution (1 mL) containing 4-[(t-butyl)dimethylsiloxy]-1-butyne (48 mg, 0.263 mmol) and then stirred for 1 hour. The solution was given a diethyl ether solution (1 mL) containing powdery p-toluenesulfonylacetylene (71 mg, 0.395 mmol). The reaction solution was heated to room temperature.

The reaction solution (at room temperature) was stirred for 3 hours and then given hydrochloric acid (1 mol/L) to suspend the reaction. The reaction product was extracted with diethyl ether. The organic layer was washed with an aqueous solution of sodium bicarbonate and then dried with anhydrous sodium sulfate. The solvent was distilled away under reduced pressure. There was obtained a crude product in the form of oily substance. The crude product was analyzed in detail by $^1$H NMR. It was found to contain no other isomers. The crude product was purified by silica gel column chromatography (n-hexane-diethyl ether). There was obtained 4-[2-((t-butyl)dimethylsiloxy)ethyl]-2-hexyl-1-(trimethylsilyl)benzene (52 mg, 50%) in the form of colorless oily substance.

$^1$H NMR: δ 0.02 (s, 6H, t-BuSiMe$_2$), 0.31 (s, 9H, SiMe$_3$), 0.80–0.95 (m, 3H, Me,), 0.89 (s, 9H, C(CH$_3$)$_3$), 1.20–1.50 (m, 6H, alkyl H), 1.50–1.68 (m, 2H, alkyl H), 2.67 (t, J=8.1 Hz, 2H, PhCH$_2$), 2.80 (t, J=7.2 Hz, 2H, PhCH$_2$), 3.81 (t, J=7.2 Hz, 2H, CH$_2$OTBS), 7.02 (d, J=7.5 Hz, 1H, Ph-H), 7.06 (s, 1H, Ph-H), 7.38 (d, J=7.5 Hz, 1H, Ph-H).

$^{13}$C NMR: δ −5.22 (t-BuSiMe$_2$), 0.37 (SiMe$_3$), 13.96, 18.24 (C(CH$_3$)$_3$), 22.53, 25.85 (C(CH$_3$)$_3$), 29.60, 31.74, 32.59, 36.30, 39.46, 64.50 (O—C), 125.82 (Ph), 129.57 (Ph), 134.64 (Ph), 135.34 (Ph), 140.12 (Ph), 148.93 (Ph).

IR (neat): 3045 (Ph), 2960, 2928, 2857, 1604, 1470, 1250 (C—Si), 1098, 837, 775 cm$^{-1}$.

Elemental analysis: calculated (C$_{23}$H$_{44}$OSi$_2$): C, 70.33%; H, 11.29%. found: C, 70.54%; H, 11.58%.

Example 15

A 74:26 mixture of 1-[2-((t-butyl)dimethylsiloxy)-ethyl]-5-hexyl-2-iodo-4-(trimethylsilyl)benzene and 5-[2-((t-butyl) dimethylsiloxy)ethyl]-1-hexyl-3-iodo-2-(trimethylsilyl)benzene The same procedure as in Example 14 was repeated except that iodine was added for reaction before the addition of hydrochloric acid (1 mol/L). There was obtained a 74:26 mixture of 1-[2-((t-butyl)dimethylsiloxy)ethyl]-5-hexyl-2-iodo-4-(trimethylsilyl)benzene and 5-[2-((t-butyl)dimethylsiloxy)ethyl]-1-hexyl-3-iodo-2-(trimethylsilyl)benzene in a 37% yield.

1-[2-((t-butyl)dimethylsiloxy)ethyl]-5-hexyl-2-iodo-4-(trimethylsilyl)benzene

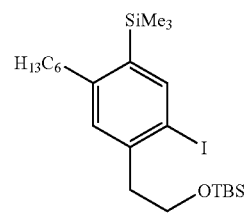

(Analyzed from a 74:26 mixture of position isomers.)

$^1$H NMR: δ 0.01 (s, 6H, t-BuSiMe$_2$), 0.29 (s, 9H, SiMe$_3$), 0.80–0.95 (m, 3H, Me), 0.87 (s, 9H, C(CH$_3$)$_3$), 1.20–1.50 (m, 6H, alkyl H), 1.60–1.72 (m, 2H, alkyl H), 2.60 (t, J=8.1 Hz, 2H, PhCH$_2$), 2.91 (t, J=7.2 Hz, 2H PhCH$_2$), 3.79 (t, J=7.2 Hz, 2H CH$_2$OTBS), 7.09, (s, 1H, Ph-H), 7.80 (s, 1H, Ph-H).

The structure was confirmed (identified) by the fact that a 12% increase in NOE due to irradiate proton at δ 0.01 ppm (SiMe$_3$) was observed in the peak at δ 7.80 ppm (Ph-H).

IR (neat): 3038 (Ph), 2954, 2927, 2856, 1591, 1524, 1463, 1379, 1360, 1250 (Si—C), 1098, 1006, 909, 837, 776, 734 cm$^{-1}$.

5-[2-((t-butyl)dimethylsiloxy)ethyl]-1-hexyl-3-iodo-2-(trimethylsilyl)benzene

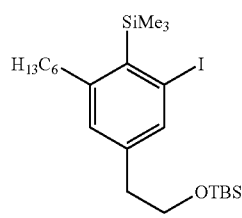

$^1$H NMR: (characteristic peaks only) δ 0.01 (s, 6H, t-BuSiMe$_2$), 0.53 (s, 9H, SiMe$_3$), 2.66 (t, J=8.1 Hz, 2H, PhCH$_2$), 2.67 (t, J=6.6 Hz, 2H, PhCH$_2$), 3.77 (t, J=6.6 Hz, 2H, CH$_2$OTBS), 6.97 (d, J=1.5 Hz, 1H, Ph-H), 7.68 (d, J=1.5 Hz, 1H, Ph-H).

Example 16

2,3-bis(cyclohexyloxy)-1,4-bis(trimethylsilyl)benzene

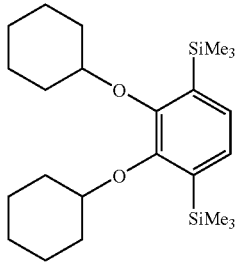

To a diethyl ether solution (1.5 mL) containing cyclohexyl (trimethylsilyl)ethynyl ether (30 mg, 0.145 mmol) and tetra-i-propoxytitanium (0.027 mL, 0.091 mmol) was added i-propylmagnesium chloride (1.42 M diethyl ether solution, 0.144 mL, 0.203 mmol) at −78° C. under an argon stream. There was obtained a homogenous yellowish solution. The solution was slowly heated to −50° C. over 30 minutes. The solution turned into dark yellowish. The solution was kept stirred for 4 hours at −50° C. The solution kept at −50° C. was given a diethyl ether solution (1 mL) containing p-toluenesulfonylacetylene in powder form (16 mg, 0.087 mmol).

The reaction solution was heated to room temperature and was stirred for 3 hours. The solution was given hydrochloric acid (1 mol/L) to suspend the reaction. The reaction product was extracted with diethyl ether. The organic layer was washed with an aqueous solution of sodium bicarbonate and then dried with anhydrous sodium sulfate. The solvent was distilled away under reduced pressure. There was obtained a crude product in the form of oily substance. The crude product was analyzed in detail by $^1$H NMR. It was found to contain no other isomers. The crude product was purified by silica gel column chromatography (n-hexane-diethyl ether). There was obtained 2,3-bis(cyclohexyloxy)-1,4-bis(trimethylsilyl)benzene (18 mg, 56%) in the form of colorless oily substance.

$^1$H NMR: δ 0.28 (s, 18H, SiMe$_3$), 1.08–1.40 (m, 10H, cyclohexyl H), 1.60 (symmetric m, 2H, cyclohexyl H), 1.75 (symmetric m, 4H, cyclohexyl H), 1.86 (symmetric m, 4H, cyclohexyl H), 4.30 (tt, J=3.9, 10.5 Hz, 2H, O—CH, 7.05 (s, 2H, Ph-H).

$^{13}$C NMR: δ 0.06 (SiMe$_3$), 24.82, 25.72, 32.69, 78.26 (O—C), 128.72 (Ph), 135.61 (Ph), 153.35 (Ph).

IR (neat): 3060 (Ph), 2933, 2857, 1590, 1451, 1363, 1344, 1245, 1221, 1196, 1177, 1127, 1043, 1019, 966, 887, 836, 758 cm$^{-1}$.

Example 17

2,3-bis(cyclohexyloxy)-5-deuterio-1,4-bis(trimethylsilyl)benzene

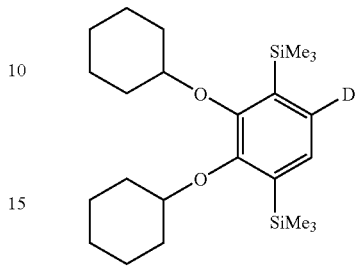

The same procedure as in Example 16 was repeated except that heavy water was added for reaction before the addition of hydrochloric acid (1 mol/L). There was obtained 2,3-bis(cyclohexyloxy)-5-deuterio-1,4-bis(trimethyl-silyl)benzene.

$^1$H NMR: δ 0.28 (s, 18H, SiMe$_3$) 1.08–1.40 (m, 10H, cyclohexyl H), 1.60 (symmetric m, 2H, cyclohexyl H), 1.75 (symmetric m, 4H, cyclohexyl H), 1.86 (symmetric m, 4H, cyclohexyl H), 4.30 (tt, J=3.9, 10.5 Hz, 2H, 0-CH), 7.05 (s, 1H, Ph-H).

An introduction of 98% deuterium was indicated by the degree of disappearance of the proton peak corresponding to δ 7.05 (Ph-H) of 2,3-bis(cyclohexyloxy)-1,4-bis(trimethylsilyl)benzene.

Example 18

2,2-bis[(benzyloxy)methyl]-4,7-bis(trimethylsilyl)indan

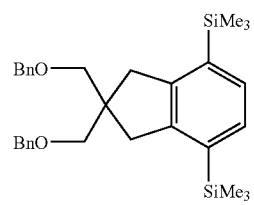

To a diethyl ether solution (4.5 mL) containing 4,4-bis[(benzyloxy)methyl]-1,7-bis(trimethylsilyl)-1,6-heptadiyne (50 mg, 0.105 mmol) and tetra-i-propoxytitanium (0.039 mL, 0.131 mmol) was added i-propylmagnesium chloride (1.49 M diethyl ether solution, 0.197 mL, 0.293 mmol) at −78° C. under an argon stream. There was obtained a homogenous yellowish solution. The solution was slowly heated to −50° C. over 30 minutes. The solution turned into dark yellowish. The solution was kept stirred for 4 hours at −50° C. The solution (kept at −50° C.) was given a diethyl ether solution (1 mL) containing p-toluenesulfonylacetylene in powder form (23 mg, 0.126 mmol).

The reaction solution was heated to room temperature and was stirred for 3 hours. The solution was given hydrochloric acid (1 mol/L) to suspend the reaction. The reaction product was extracted with diethyl ether. The organic layer was washed with an aqueous solution of sodium bicarbonate and then dried with anhydrous sodium sulfate. The solvent was distilled away under reduced pressure. There was obtained a crude product in the form of oily substance. The crude product was purified by silica gel column chromatography (n-hexane-diethyl ether). There was obtained 2,2-bis[(benzyloxy)methyl]-4,7-bis(trimethylsilyl)indan (39 mg, 74%) in the form of colorless oily substance.

$^1$H NMR: δ 0.28 (s, 18H, SiMe$_3$), 2.90 (s, 4H, PhCH$_2$), 3.52 (s, 4H, CH$_2$OBn), 4.53 (s, 4H, PhCH$_2$O), 7.22–7.35 (m, 12H, Ph-H).

$^{13}$C NMR: δ −0.97 (SiMe$_3$), 39.65, 47.69, 73.22, 73.44, 127.46 (Ph), 127.55 (o- or m-Ph), 128.36 (m- or o-Ph), 131.29 (Ph), 136.87 (Ph), 138.98 (Ph), 146.75 (Ph).

IR (neat): 3090 (Ph), 3060 (Ph), 3033 (Ph), 2953, 2895, 2852, 1496, 1453, 1359, 1249 (SiMe$_3$), 1198, 1100, 1028, 892, 836, 751, 696 cm$^{-1}$.

Elemental analysis: calculated (C$_{31}$H$_{42}$O$_2$Si$_2$): C, 74.05%; H, 8.42%. found: C, 73.89%; H, 8.35%.

Example 19

N-benzyl-4,7-bis(trimethylsilyl)-1-isoindolinone

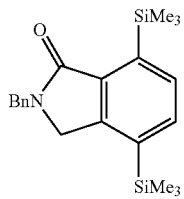

To a diethyl ether solution (1.5 mL) containing N-benzyl-N-[3-(trimethylsilyl)-2-propinyl]-3-(trimethylsilyl)-2-propinamide (30 mg, 0.088 mmol) and tetra-i-propoxytitanium (0.039 mL, 0.132 mmol) was added i-propylmagnesium chloride (1.48 M diethyl ether solution, 0.179 mL, 0.263 mmol) at −78° C. under an argon stream. There was obtained a homogenous yellowish solution. The solution was slowly heated to −30° C. over 30 minutes. The solution turned into reddish. The solution was kept stirred for 4 hours at −30° C. The solution (kept at −30° C.) was given a diethyl ether solution (1 mL) containing p-toluenesulfonylacetylene (19 mg, 0.105 mmol) in powder form.

The reaction solution was heated to room temperature and was stirred for 3 hours. The solution was given hydrochloric acid (1 mol/L) to suspend the reaction. The reaction product was extracted with diethyl ether. The organic layer was washed with an aqueous solution of sodium bicarbonate and then dried with anhydrous sodium sulfate. The solvent was distilled away under reduced pressure. There was obtained a crude product in the form of oily substance. The crude product was purified by silica gel column chromatography (n-hexane-ethyl acetate). There was obtained N-benzyl-4,7-bis(trimethylsilyl)-1-isoindolinone (24 mg, 88%) in the form of colorless oily substance.

$^1$H NMR: δ 0.27 (s, 9H, SiMe$_3$), 0.44 (s, 9H, SiMe$_3$), 4.29 (s, 2H, PhCH$_2$N), 4.81 (s, 2H, PhCH$_2$N), 7.27–7.39 (m, 5H, Ph-H), 7.59 (d, J=7.2 Hz, 1H, Ph-H), 7.63 (d, J=7.2 Hz, 1H, Ph-H).

$^{13}$C NMR: δ −0.96 (SiMe$_3$), −0.61 (SiMe$_3$), 46.31, 50.49, 127.62 (Ph), 128.09 (o- or m-Ph), 128.83 (m- or o-Ph), 133.70 (Ph), 135.09 (Ph), 135.84 (Ph), 136.09 (Ph), 137.36 (Ph), 139.75 (Ph), 146.25 (Ph), 169.59 (C=O).

IR (neat): 3050 (Ph), 3030 (Ph), 2953, 1688 (C=O), 1640, 1540, 1496, 1452, 1410, 1358, 1320, 1293, 1250 (SiMe$_3$), 1193, 1028, 944, 919, 840, 751, 696 cm$^{-1}$.

Elemental analysis: calculated (C$_{21}$H$_{29}$NOSi): C, 68.61%; H, 7.95%; N, 3.81%. found: C, 68.40%; H, 7.87%; N, 3.75%.

Example 20

5-(t-butoxycarbonyl)-6-hexylindan

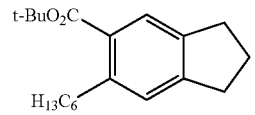

(1,6-heptadiynyl p-tolylsulfone)

First, 1,6-heptadiynyl p-tolylsulfone as a starting material was synthesized according to the following scheme.

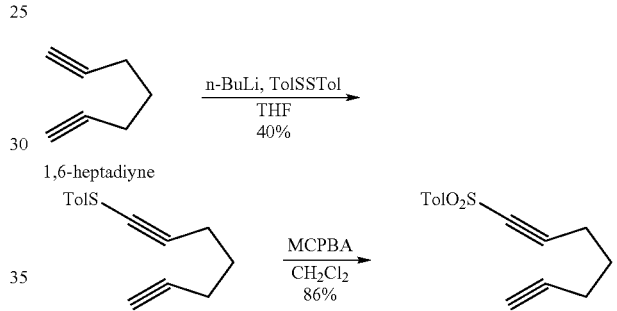

$^1$H NMR: δ 1.76 (quintet, J=6.9 Hz, 2H, alkyl H), 1.96 (t, J=2.4 Hz, 1H, C≡CH), 2.25 (dt, J=2.4, 6.9 Hz, 2H, CH$_2$C≡CH), 2.46 (s, 3H, PhMe), 2.51 (t, J=6.9 Hz, 2H, CH$_2$C≡CSO$_2$Tol), 7.37 (d, J=8.4 Hz, 2H, Ph-H), 7.87 (d, J=8.4 Hz, 2H, Ph-H).

$^{13}$C NMR: δ 17.65, 17.94, 21.80, 25.91, 69.77 (C≡C), 78.81 (C≡C), 82.18 (C≡C), 95.71 (C≡C), 127.21 (o- or m-Ph), 129.79 (m- or o-Ph), 138.78 (p-Ph), 145.08 (ipso-Ph).

IR (neat): 3289 (Ph), 3058 (Ph), 2940, 2201 (C≡C), 1595, 1431, 1327 (S=O), 1158 (S=O), 1089, 1048, 814 cm$^{-1}$.

Elemental analysis: calculated (C$_{14}$H$_{14}$O$_2$S): C, 68.26%; H, 5.73%. found: C, 67.93%; H, 5.53%.

To a diethyl ether solution (1.5 mL) containing t-butyl 2-nonyonate (20 mg, 0.095 mmol) and tetra-i-propoxytitanium (0.035 mL, 0.119 mmol) was added i-propylmagnesium chloride (1.48 M diethyl ether solution, 0.180 mL, 0.267 mmol) at −78° C. under an argon stream. There was obtained a homogenous yellowish solution. The solution was slowly heated to −50° C. over 30 minutes. The solution turned into reddish. The solution was kept stirred for 5 hours at −50° C. The solution (kept at −50° C.) was given a diethyl ether solution (1 mL) containing 1,6-heptadinyl p-tolylsulfone (19 mg, 0.076 mmol) and the solution was stirred at −50° C. for 3 hours.

The reaction solution was heated to room temperature and was stirred for 3 hours. The solution was given hydrochloric acid (1 mol/L) to suspend the reaction. The reaction product was extracted with diethyl ether. The organic layer was washed with an aqueous solution of sodium bicarbonate and then dried with anhydrous sodium sulfate. The solvent was distilled away under reduced pressure. There was obtained a crude product in the form of oily substance. The crude product was purified by silica gel column chromatography (n-hexane-diethyl ether). There was obtained 5-(t-butoxycarbonyl)-6-hexylindan (17 mg, 74%) in the form of colorless oily substance.

$^1$H NMR: δ 0.88 (t, J=6.9 Hz, 3H, Me), 1.20–1.55 (m, 8H, alkyl H), 1.58 (s, 9H, C(CH$_3$)$_3$), 2.06 (quintet, J=7.2 Hz, 2H, cyclopentyl H), 2.86 (t, J=7.2 Hz, 2H, PhCH$_2$), 2.88 (t, J=7.2 Hz, 4H, PhCH$_2$), 7.06 (s, 1H, Ph-H), 7.58 (s, 1H, Ph-H).

$^{13}$C NMR: δ 13.98, 22.52, 25.35, 28.15 (C(CH$_3$)$_3$), 29.41, 31.75, 32.14, 32.20, 32.76, 34.32, 80.70 (CO$_2$C), 125.91 (Ph), 126.56 (Ph), 130.04 (Ph), 141.65 (Ph), 141.75 (Ph), 147.89 (Ph), 168.27 (C=O).

IR (neat): 3005 (Ph), 2960, 2927, 2845, 1716 (C=O), 1458, 1390, 1366, 1278, 1255, 1167, 1118, 1022, 885, 856, 800 cm$^{-1}$.

Elemental analysis: calculated (C$_{20}$H$_{30}$O$_2$): C, 79.42%; H, 10.00%. found: C, 79.19%; H, 10.10%.

Example 21

5-(t-butoxycarbonyl)-4-deuterio-6-hexylindan

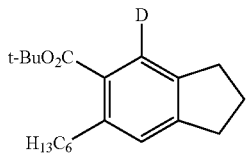

The same procedure as in Example 20 was repeated except that heavy water was added for reaction before the addition of hydrochloric acid (1 mol/L). There was obtained 5-(t-butoxycarbonyl)-4-deuterio-6-hexylindan.

$^1$H NMR: δ 0.88 (t, J=6.9 Hz, 3H, Me), 1.20–1.55 (m, 8H, alkyl H), 1.58 (s, 9H, C(CH$_3$)$_3$), 2.06 (quintet, J=7.2 Hz, 2H, cyclopentyl H), 2.86 (t, J=7.2 Hz, 2H, PhCH$_2$), 2.88 (t, J=7.2 Hz, 4H, PhCH$_2$), 7.06 (s, 1H, Ph-H).

An introduction of 91% deuterium was indicated by the degree of disappearance of the proton peak corresponding to δ 7.58 (Ph-H) of 5-(t-butoxycarbonyl)-6-hexylindan.

Examples 22 and 23

The same procedure as in Example 20 was repeated to give the following compounds except that the acetylene compound and diyne compound were replaced.

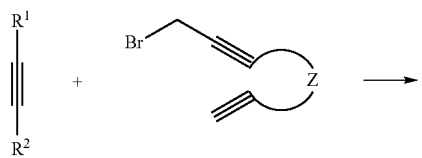

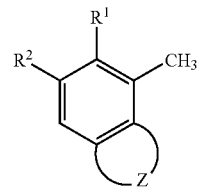

TABLE 1

| Example | R$^1$ | R$^2$ | Z | Yield (%) |
|---|---|---|---|---|
| 22 | CO$_2$Et | Me | CH$_2$C(CH$_2$OBn)$_2$CH$_2$ | 60 |
| 23 | CONEt$_2$ | C$_6$H$_{13}$ | (CH$_2$)$_3$ | 73 |

Example 24

3,4-dibutylphenyl p-tolylsulfoxide

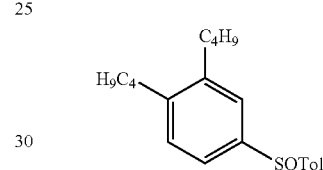

To a diethyl ether solution (1.5 mL) containing 5-decyne (0.020 mL, 0.111 mmol) and tetra-i-propoxytitanium (0.041 mL, 0.139 mmol) was added i-propylmagnesium chloride (1.35 M diethyl ether solution, 0.231 mL, 0.312 mmol) at −78° C. under an argon stream. There was obtained a homogenous yellowish solution. The solution was slowly heated to −50° C. over 30 minutes. The solution turned into blackish. The solution was kept stirred for 2 hours at −50° C. The solution (kept at −50° C.) was given a diethyl ether solution (1 mL) containing p-toluenesulfinylacetylene (37 mg, 0.223 mmol) and the solution was stirred at −50° C. for 1 hour.

The reaction solution was heated to −20° C. and then stirred for 7 hours. The solution was given hydrochloric acid (1 mol/L) to suspend the reaction. The reaction product was extracted with diethyl ether. The organic layer was washed with an aqueous solution of sodium bicarbonate and then dried with anhydrous sodium sulfate. The solvent was distilled away under reduced pressure. There was obtained a crude product in the form of oily substance. The crude product was analyzed in detail by $^1$H NMR. It was found to contain no other isomers. The crude product was purified by silica gel column chromatography (n-hexane-ethyl acetate). There was obtained 3,4-dibutylphenyl p-tolylsulfoxide (18 mg, 50%) in the form of colorless oily substance.

$^1$H NMR: δ 0.91 (t, J=7.2 Hz, 3H, Me), 0.92 (t, J=7.2 Hz, 3H, Me), 1.36 (sextet, J=7.2 Hz, 4H, alkyl H), 1.45–1.60 (m, 4H, alkyl H), 2.35 (s, 3H, PhMe), 2.58 (t, J=7.2 Hz, 2H, PhCH$_2$), 2.61 (t, J=7.2 Hz, 2H, PhCH$_2$), 7.19 (d, J=8.1 Hz, 1H, Ph-H), 7.25 (d, J=8.1 Hz, 2H, Ph-H), 7.30 (dd, J=1.8, 8.1 Hz, 1H, Ph-H), 7.43 (d, J=1.8 Hz, 1H, Ph-H), 7.52 (d, J=8.1 Hz, 2H, Ph-H).

$^{13}$C NMR: δ 13.81 (2 peaks), 21.27, 22.58, 22.64, 32.19, 32.27, 32.96, 33.05, 122.34 (Ph), 125.00 (o- or m-Ph), 125.44 (Ph), 129.98 (m- or o-Ph), 130.08 (Ph), 141.37 (Ph), 142.12 (Ph), 142.64 (Ph), 142.84 (Ph), 144.20 (Ph).

IR (neat): 3033 (Ph), 2959, 2925, 2862, 1735, 1720, 1655, 1595, 1458, 1400, 1380, 1305, 1090, 1048 (S=O), 970, 808 cm$^{-1}$.

Example 25 t-butyl 5-hexyl-4-methyl-2-(trimethylsilyl)benzoate

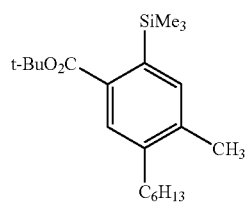

To a diethyl ether solution (3 mL) containing t-butyl 3-(trimethylsilyl)-2-propinoate (50 mg, 0.252 mmol) and tetra-i-propoxytitanium (0.093 mL, 0.315 mmol) was added i-propylmagnesium chloride (1.47 M diethyl ether solution, 0.480 mL, 0.706 mmol) at −78° C. under an argon stream. There was obtained a homogenous yellowish solution. The solution was slowly heated to −50° C. over 30 minutes. The solution turned into reddish. The solution was kept stirred for 5 hours at −50° C. The solution (kept at −50° C.) was given 1-octyne (0.030 mL, 0.202 mmol), and the solution was stirred for 3 hours.

The solution was given propargylbromide (0.028 mL, 0.378 mmol). The reaction solution was heated to room temperature and stirred for 4 hours at room temperature. The solution was given hydrochloric acid (1 mol/L) to suspend the reaction. The reaction product was extracted with diethyl ether. The organic layer was washed with an aqueous solution of sodium bicarbonate and then dried with anhydrous sodium sulfate. The solvent was distilled away under reduced pressure. There was obtained a crude product in the form of oily substance. The crude product underwent preparative silica gel thin-layer chromatography (n-hexane-diethyl ether). There was obtained t-butyl 5-hexyl-4-methyl-2-(trimethylsilyl)benzoate (37 mg, 52%) in the form of colorless oily substance.

Examples 26 and 27

The same procedure as in Example 25 was repeated to give the following compounds except that the acetylene compound was replaced.

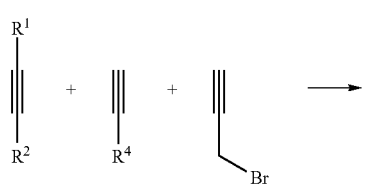

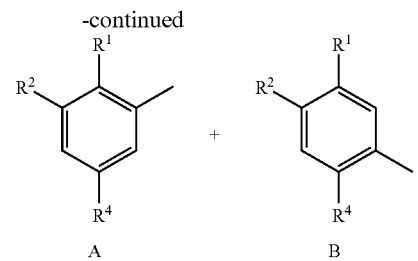

TABLE 2

| Example | R$^1$ | R$^2$ | R$^4$ | A | B |
|---|---|---|---|---|---|
| 26 | SiMe$_3$ | CO$_2$t-Bu | (branched alkenyl chain) | — | 53% |
| 27 | SiMe$_3$ | C$_6$H$_{13}$ | (CH$_2$)$_2$OBn | 35% | — |

Example 28

The same procedure as in Example 27 was repeated except that heavy water was added for reaction before the addition of hydrochloric acid (1 mol/L). There was obtained a compound represented by the formula below in which deuteration took place at the benzyl position. Incidentally, the ratio of introduction of deuterium was quantitative.

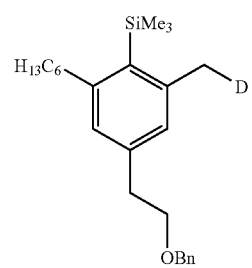

Example 29

2,2-bis[(benzyloxy)methyl]-5-methyl-4,7-bis(trimethylsilyl)indan

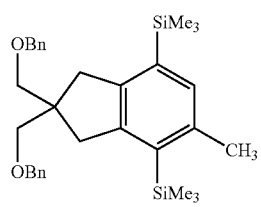

To a diethyl ether solution (2 mL) containing 4,4-bis[(benzyloxy)methyl]-1,7-bis(trimethylsilyl)-1,6-heptadiyne (50 mg, 0.104 mmol) and tetra-i-propoxytitanium (0.039 mL, 0.131 mmol) was added i-propylmagnesium chloride (1.53 M diethyl ether solution, 0.185 mL, 0.282 mmol) at −78° C. under an argon stream. There was obtained a homogenous yellowish solution. The solution was slowly heated to −50° C. over 30 minutes. The solution was kept stirred for 4 hours at −50° C. The solution (kept at −50° C.) was given propargylbromide (0.012 mL, 0.157 mmol).

The reaction solution was heated to room temperature and stirred for 4 hours. The solution was given hydrochloric acid (1 mol/L) to suspend the reaction. The reaction product was extracted with diethyl ether. The organic layer was washed with an aqueous solution of sodium bicarbonate and then dried with anhydrous sodium sulfate. The solvent was distilled away under reduced pressure. There was obtained a crude product in the form of oily substance. The crude product underwent preparative silica gel thin-layer chromatography (n-hexane-diethyl ether). There was obtained 2,2-bis[(benzyloxy)methyl]-5-methyl-4,7-bis(trimethylsilyl)indan (40 mg, 73%) in the form of colorless oily substance.

Examples 30 to 34

The same procedure as in Example 29 was repeated to give the following compounds except that the acetylene compound or electrophilic reagent was replaced.

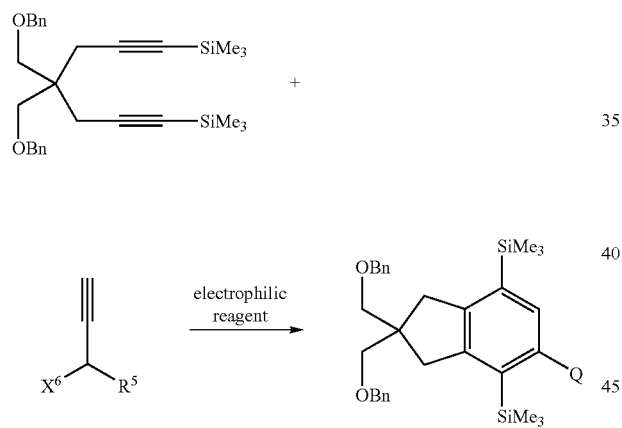

TABLE 3

| Example | R⁵ | X⁶ | Electrophilic reagent | Q | Yield (%) |
|---|---|---|---|---|---|
| 30 | H | Cl | H⁺ | CH₃ | 60 |
| 31 | Me | Br | H⁺ | CH₃ | 31 |
| 32 | H | Br | I₂ | ⟍⟋I | 72 |
| 33 | H | Br | O₂ | ⟍⟋OH | 43 |
| 34 | H | Br | ≡—CH₂Br/Cu⁺ | ⟍⟋= | 42 |

Example 35

N,N-diethyl-3-hexyl-5-phenyl-2-picolinamide

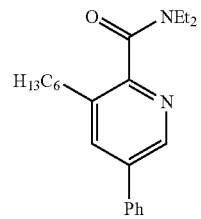

To a diethyl ether solution (1.5 mL) containing N,N-diethyl-2-nonyneamide (48 mg, 0.229 mmol) and tetra-i-propoxytitanium (0.084 mL, 0.285 mmol) was added i-propylmagnesium chloride (1.53 M diethyl ether solution, 0.418 mL, 0.637 mmol) at −78° C. under an argon stream. There was obtained a homogenous yellowish solution. The solution was slowly heated to −50° C. over 30 minutes. The solution turned into reddish. The solution was kept stirred for 5 hours at −50° C. The solution (kept at −50° C.) was given ethynylbenzene (0.020 mL, 0.182 mmol). The solution was stirred for 3 hours.

Then, the solution was given p-toluenesulfonylcyanide (49 mg, 0.273 mmol) in powder form. The solution was stirred at −50° C. for 3 hours and then given water to suspend the reaction. The solution was given anhydrous sodium sulfate. Precipitates were filtered off through Celite, and the solvent was distilled away under reduced pressure. There was obtained a crude product in the form of oily substance. The crude product was purified by silica gel column chromatography (n-hexane-ethyl acetate). There was obtained N,N-diethyl-3-hexyl-5-phenyl-2-picolinamide (43 mg, 70%). in the form of colorless oily substance.

Example 36

N,N-diethyl-3-hexyl-5-phenyl-6-iodo-2-picolinamide

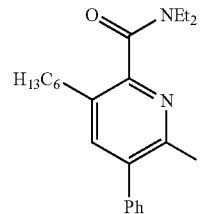

The same procedure as in Example 35 was repeated except that iodine was added before water was added to suspend the reaction. There was obtained N,N-diethyl-3-hexyl-5-phenyl-6-iodo-2-picolinamide in a 70% yield.

Examples 37 to 40

The same procedure as in Example 35 was repeated to give the following compounds except that the acetylene compound was replaced and the reaction temperature (for reaction of p-toluenesulfonecyanide) was changed.

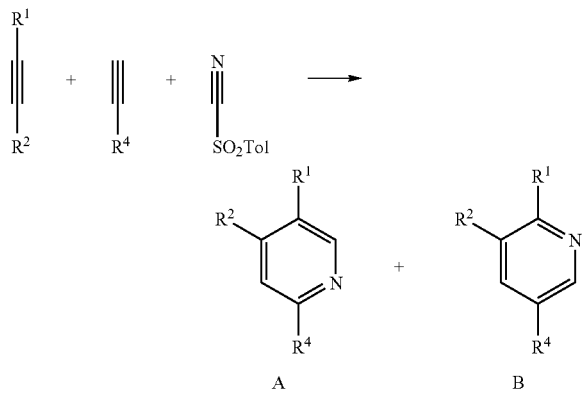

TABLE 4

| Example | R$^1$ | R$^2$ | R$^4$ | Reaction temperature (° C.) | A | B |
|---|---|---|---|---|---|---|
| 37 | CONEt$_2$ | C$_6$H$_{13}$ | C$_6$H$_{13}$ | −50 | — | 63% |
| 38 | CONEt$_2$ | C$_6$H$_{13}$ | SiMe$_3$ | −50 | — | 55% |
| 39 | CO$_2$t—Bu | C$_6$H$_{13}$ | C$_6$H$_{13}$ | −50 | — | 28% |
| 40 | CO$_2$t—Bu | C$_6$H$_{13}$ | C$_6$H$_{13}$ | −10 | — | 50% |

Example 41

2-[2-(benzyloxy)ethyl]-4,5-dibutylpyridine

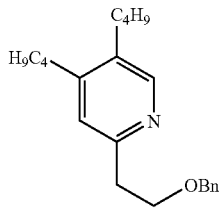

To a diethyl ether solution (1.5 mL) containing 5-decyne (0.020 mL, 0.111 mmol) and tetra-i-propoxytitanium (0.41 mL, 0.139 mmol) was added i-propylmagnesium chloride (1.36 M diethyl ether solution, 0.229 mL, 0.312 mmol) at −78° C. under an argon stream. There was obtained a homogenous yellowish solution. The solution was slowly heated to −50° C. over 30 minutes. The solution turned into blackish. The solution was kept stirred for 3 hours at −50° C. The solution (kept at −50° C.) was given a diethyl ether solution (1 mL) of 4-benzyloxy-1-butyne (14 mg, 0.089 mmol). The solution was stirred for 2 hours.

Then, the solution was given a diethyl ether solution (1 mL) containing p-toluenesulfonylcyanide in powder form (24 mg, 0.134 mmol). The reaction solution was heated to −10° C. The solution was stirred at −10° C. for 3 hours and then given water to suspend the reaction. The solution was given anhydrous sodium sulfate. Precipitates were filtered off through Celite, and the solvent was distilled away under reduced pressure. There was obtained a crude product in the form of oily substance. The crude product was purified by silica gel column chromatography (n-hexane-ethyl acetate). There was obtained 2-[2-(benzyloxy)ethyl]-4,5-dibutyl-pyridine (16 mg, 55%) in the form of colorless oily substance.

The present invention permits efficient production of an organotitanium compound capable of regioselectively converting a substituted acetylene compound into polysubstituted benzene or polysubstituted pyridine. The present invention also permits efficient production of a variety of polysubstituted benzene and polysubstituted pyridine useful for pharmaceuticals and agricultural chemicals and intermediates thereof by various addition reactions on the titanium compound.

The invention claimed is:

1. A process for producing an organotitanium compound which comprises reacting an acetylene compound represented by the formula (8) below in the presence of a titanium compound represented by the formula (2) below and a Grignard reagent represented by the formula (3) below with a compound represented by the formula (5) below, thereby giving said titanium compound represented by the formula (9) and/or (10) below

where R$^1$ denotes a C$_{1-20}$ alkyl group {which may be substituted with a C$_{1-6}$ alkoxy group (which may be substituted with a phenyl group) or OSiR$^7$R$^8$R$^9$ (where R$^7$, R$^8$, and R$^9$ denote mutually independently a C$_{1-6}$ alkyl group or phenyl group)}, C$_{3-20}$ alkenyl group, C$_{1-6}$ alkoxy group, C$_{1-6}$ alkoxycarbonyl group, C$_{1-6}$ alkylaminocarbonyl group, di-C$_{1-6}$-alkyaminocarbonyl group, phenyl group (which may be substituted with a C$_{1-6}$ alkyl group, C$_{1-6}$ alkoxy group, C$_{1-6}$ alkoxycarbonyl group, C$_{1-6}$ alkylaminocarbonyl group, or di-C$_{1-6}$-alkylaminocarbonyl group), furyl group, amino group, SiR$^7$R$^8$R$^9$ (where R$^7$, R$^8$, and R$^9$ are defined as above), or SnR$^{10}$R$^{11}$R$^{12}$ (where R$^{10}$, R$^{11}$, and R$^{12}$ denote mutually independently a halogen atom, C$_{1-6}$ alkyl group, or phenyl group); R$^4$ denotes a hydrogen atom, C$_{1-20}$ alkyl group, C$_{1-6}$ alkoxy group, C$_{1-6}$ alkoxycarbonyl group, C$_{1-6}$ alkylaminocarbonyl group, di-C$_{1-6}$-alkylaminocarbonyl group, phenyl group (which may be substituted with a C$_{1-6}$ alkyl group, C$_{1-6}$ alkoxy group, C$_{1-6}$ alkoxycarbonyl group, C$_{1-6}$ alkylaminocarbonyl group, or di-C$_{1-6}$-alkylaminocarbonyl group), furyl group, amino group, SiR$^7$R$^8$R$^9$ (where R$^7$, R$^8$, and R$^9$ are defined as above), or SnR$^{10}$R$^{11}$R$^{12}$ (where R$^{10}$, R$^{11}$, and R$^{12}$ are defined as above); and Y denotes Z$^1$-Z$^2$-Z$^3$ or Z$^4$-Z$^5$-Z$^6$-Z$^7$ {where Z$^1$, Z$^3$, Z$^4$, Z$^5$, and Z$^7$ denote mutually independently C═O or CR$^{14}$R$^{15}$ (where R$^{14}$ and R$^{15}$ denote mutually independently a hydrogen atom or C$_{1-6}$ alkyl group (which may be substituted with a C$_{1-6}$ alkoxy group (which may be substituted with a phenyl group) or OSiR$^7$R$^8$R$^9$ (where R$^7$, R$^8$, and R$^9$ are defined as above))>, Z$^2$ and Z$^6$ denote mutually independently O, S, C═O, NR$^{16}$ <where R$^{16}$ denotes a C$_{1-6}$ alkyl group (which may be substituted with a C$_{1-6}$ alkoxy group (which may be substituted with a C$_{1-6}$ alkoxy group (which may be substituted with a phenyl group) or OSiR$^7$R$^8$R$^9$ (where R$^7$, R$^8$, and R$^9$ are defined as above))>, or $CR^{14'}R^{15'}$ (where $R^{14'}$ and $R^{15'}$ denote mutually independently a hydrogen atom or $C_{1-6}$ alkyl group (which may be substituted with a $C_{1-6}$ alkoxy group (which may be substituted with a phenyl group) or $OSiR^7R^8R^9$ (where $R^7$, $R^8$, and $R^9$ are defined as above))>}

where $X^1$, $X^2$, $X^3$, and $X^4$ denote mutually independently a halogen atom, $C_{1-6}$ alkoxy group {which may be substituted with a phenyl group (which may be substituted with a $C_{1-6}$ alkyl group, $C_{1-6}$ alkoxy group, or phenyl group), or a naphthyl group)}, phenoxy group (which may be substituted with a $C_{1-6}$ alkyl group, $C_{1-6}$ alkoxy group, or phenyl group), or naphthoxy group

where R denotes a $C_{2-8}$ alkyl group having a hydrogen atom at the β position, and $X^5$ denotes a halogen atom

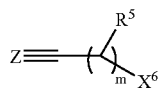

where $R^5$ denotes a hydrogen atom, $C_{1-20}$ alkyl group, or phenyl group (which may be substituted with a $C_{1-6}$ alkyl group, $C_{1-6}$ alkoxy group, $C_{1-6}$ alkoxycarbonyl group, $C_{1-6}$ alkylaminocarbonyl group, or di-$C_{1-6}$-alkylaminocarbonyl group), Z denotes CR' (where R' denotes a hydrogen atom or $C_{1-20}$ alkyl group) or a nitrogen atom; $X^6$ denotes a halogen atom, $C_{1-6}$ alkoxy group {which may be substituted with a phenyl group (which may be substituted with a $C_{1-6}$ alkyl group, $C_{1-6}$ alkoxy group, and phenyl group), or naphthyl group}, phenoxy group (which may be substituted with a $C_{1-6}$ alkyl group, $C_{1-6}$ alkoxy group, or phenyl group), naphthoxy group, $SO_nR^6$ {where $R^6$ denotes a $C_{1-6}$ alkyl group or phenyl group (which may be substituted with a halogen atom or $C_{1-6}$ alkyl group) and n denotes 1 or 2}, $OSO_2R^6$ (where $R^6$ is defined as above), or $OP(O)(OR^{13})_2$ group (where $R^{13}$ denotes a $C_{1-6}$ alkyl group); and m denotes 0 or 1 where $R^1$, $R^4$, $R^5$, Y, Z, $X^6$, and m are defined as above; and $X^p$ and $X^q$ denote any of $X^1 \sim X^4$ (which are defined as above).

2. A process for producing an organotitanium compound which comprises reacting an acetylene compound represented by the formula (1) below in the presence of a titanium compound represented by the formula (2) below and a Grignard reagent represented by the formula (3) below with a compound represented by the formula (11) below, thereby giving said titanium compound represented by the formula (12) below

where $R^1$ and $R^2$ denote mutually independently a $C_{1-20}$ alkyl group {which may be substituted with a $C_{1-6}$ alkoxy group (which may be substituted with a phenyl group) or $OSiR^7R^8R^9$ (where $R^7$, $R^8$, and $R^9$ denote mutually independently a $C_{1-6}$ alkyl group or phenyl group)}, $C_{3-20}$ alkenyl group, $C_{1-6}$ alkoxy group, $C_{1-6}$ alkoxycarbonyl group, $C_{1-6}$ alkylaminocarbonyl group, di-$C_{1-6}$-alkyaminocarbonyl group, phenyl group (which may be substituted with a $C_{1-6}$ alkyl group, $C_{1-6}$ alkoxy group, $C_{1-6}$ alkoxycarbonyl group, $C_{1-6}$ alkylaminocarbonyl group, or di-$C_{1-6}$-alkylaminocarbonyl group), furyl group, amino group, $SiR^7R^8R^9$ (where $R^7$, $R^8$, and $R^9$ are defined as above), or $SnR^{10}R^{11}R^{12}$ (where $R^{10}$, $R^{11}$, and $R^{12}$ denote mutually independently a halogen atom, $C_{1-6}$ alkyl group, or phenyl group)

where $X^1$, $X^2$, $X^3$, and $X^4$ denote mutually independently a halogen atom, $C_{1-6}$ alkoxy group {which may be substituted with a phenyl group (which may be substituted with a $C_{1-6}$ alkyl group, $C_{1-6}$ alkoxy group, or phenyl group), or a naphthyl group)}, phenoxy group (which may be substituted with a $C_{1-6}$ alkyl group, $C_{1-6}$ alkoxy group, or phenyl group), or naphthoxy group

where R denotes a $C_{2-8}$ alkyl group having a hydrogen atom at the β position, and $X^5$ denotes a halogen atom

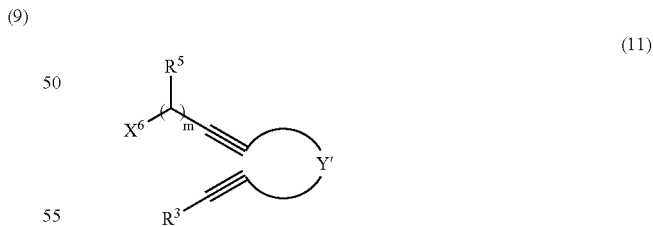

where $R^3$ denotes a hydrogen atom, $C_{1-20}$ alkyl group, $C_{1-6}$ alkoxy group, $C_{1-6}$ alkoxycarbonyl group, $C_{1-6}$ alkylaminocarbonyl group, di-$C_{1-6}$-alkylaminocarbonyl group, phenyl group (which may be substituted with a $C_{1-6}$ alkyl group, $C_{1-6}$ alkoxy group, $C_{1-6}$ alkoxycarbonyl group, $C_{1-6}$ alkylaminocarbonyl group, or di-$C_{1-6}$-alkylaminocarbonyl group), furyl group, amino group, $SiR^7R^8R^9$ ($R^7$, $R^8$, and $R^9$ are defined as above), or $SnR^{10}R^{11}R^{12}$ (where $R^{10}$, $R^{11}$, $R^{12}$ are defined as above); $R^5$ denotes a hydrogen atom, $C_{1-20}$ alkyl group, or phenyl group (which may be substituted with a $C_{1-6}$ alkyl group, $C_{1-6}$ alkoxy group, $C_{1-6}$ alkoxycarbonyl group, $C_{1-6}$ alkylaminocarbonyl group, or di-$C_{1-6}$-alkylaminocarbonyl group); Y' denotes $Z^1$-$Z^2$-$Z^3$ or $Z^4$-$Z^5$-$Z^6$-$Z^7$ {where $Z^1$, $Z^3$, $Z^4$, $Z^5$, and $Z^7$ denote mutually independently C=O or $CR^{14}R^{15}$ <where $R^{14}$ and $R^{15}$ denote mutually independently a hydrogen atom or $C_{1-6}$ alkyl group (which may be substituted with a $C_{1-6}$ alkoxy group (which may be substituted with a phenyl group) or $OSiR^7R^8R^9$ (where $R^7$, $R^8$, and $R^9$ are defined as above))>, $Z^2$ and $Z^6$ denote mutually independently O, S, C=O, $NR^{16}$ (where $R^{16}$ denotes a $C_{1-6}$ alkyl group (which may be substituted with $C_{1-6}$ alkoxy group (which may be substituted with a phenyl group)) or $OSiR^7R^8R^9$ (where $R^7$, $R^8$, and $R^9$ are defined as above)>, or $CR^{14'}R^{15'}$ <where $R^{14'}$ and $R^{15'}$ denote mutually independently a hydrogen atom, $C_{1-6}$ alkyl group (which may be substituted with a $C_{1-6}$ alkoxy group (which may be substituted with a phenyl group) or $OSiR^7R^8R^9$ (where $R^7$, $R^8$, and $R^9$ are defined as above))>}; $X^6$ denotes a halogen atom, $C_{1-6}$ alkoxy group {which may be substituted with a phenyl group (which may be substituted with a $C_{1-6}$ alkyl group, $C_{1-6}$ alkoxy group, or phenyl group), or naphthyl group}, phenoxy group (which may be substituted with a $C_{1-6}$ alkyl group, $C_{1-6}$ alkoxy group, or phenyl group), naphthoxy group, $SO_nR^6$ {where $R^6$ denotes a $C_{1-6}$ alkyl group or phenyl group (which may be substituted with a halogen atom or $C_{1-6}$ alkyl group), and n denotes 1 or 2}, $OSO_2R^6$ (where $R^6$ is defined as above), or $OP(O)(OR^{13})_2$ group (where $R^{13}$ denotes a $C_{1-6}$ alkyl group); and m denotes 0 or 1

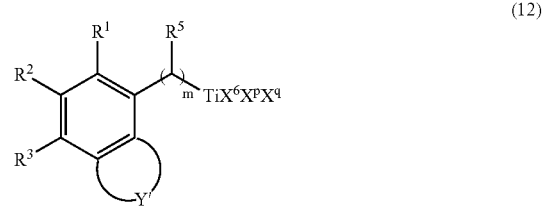

(12)

where $R^1$ to $R^3$, $R^5$, Y', $X^6$, and m are defined as above; and $X^p$ and $X^q$ denote any of $X^1$~$X^4$ (which are defined as above).

3. A process for producing an organotitanium compound as defined in claim 1 or 2, wherein the titanium compound is tetra-i-propoxytitanium.

4. A process for producing an organotitanium compound as defined in claim 1 or 2, wherein the Grignard reagent is an i-propyl Grignard reagent.

5. A process for addition reaction which comprises adding to the organotitanium compound obtained by the process defined in claim 1 or 2 a compound having an aldehyde group, ketone group, imino group, aliphatic double bond, aliphatic triple bond, acyl group or ester group or an electrophilic reagent of water, heavy water, iodine or oxygen, and performing addition reaction on the organotitanium compound to produce a polysubstituted fused bicyclic compound containing a benezene or a pyridine ring as a one of the fused rings.

* * * * *